United States Patent
Tarran et al.

(10) Patent No.: US 10,894,811 B2
(45) Date of Patent: Jan. 19, 2021

(54) PEPTIDE INHIBITORS OF CALCIUM CHANNELS

(71) Applicant: The University of North Carolina at Chapel Hill, Chapel Hill, NC (US)

(72) Inventors: Robert Tarran, Chapel Hill, NC (US); Tongde Wu, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 23 days.

(21) Appl. No.: 16/078,397

(22) PCT Filed: Feb. 22, 2017

(86) PCT No.: PCT/US2017/018840
§ 371 (c)(1),
(2) Date: Aug. 21, 2018

(87) PCT Pub. No.: WO2017/147128
PCT Pub. Date: Aug. 31, 2017

(65) Prior Publication Data
US 2019/0062386 A1 Feb. 28, 2019

Related U.S. Application Data

(60) Provisional application No. 62/298,204, filed on Feb. 22, 2016.

(51) Int. Cl.
C07K 14/47 (2006.01)
C07K 14/435 (2006.01)
A61P 37/08 (2006.01)
A61P 37/06 (2006.01)
A61K 38/00 (2006.01)
A61K 9/00 (2006.01)

(52) U.S. Cl.
CPC .......... *C07K 14/4702* (2013.01); *A61P 37/06* (2018.01); *A61P 37/08* (2018.01); *C07K 14/435* (2013.01); *A61K 9/0078* (2013.01); *A61K 38/00* (2013.01)

(58) Field of Classification Search
None
See application file for complete search history.

(56) References Cited

U.S. PATENT DOCUMENTS

2004/0110938 A1* 6/2004 Parekh .................. C07K 14/47
536/23.5
2014/0228276 A1* 8/2014 Tarran .................. C07K 14/435
514/1.7

FOREIGN PATENT DOCUMENTS

WO 2013/043720 A1 3/2013

OTHER PUBLICATIONS

Sigma "Designing peptides" accessed from sigmaaldrich.com on Nov. 21, 2019 (Year: 2019).*

(Continued)

*Primary Examiner* — Adam Weidner
(74) *Attorney, Agent, or Firm* — Myers Bigel, P.A.

(57) ABSTRACT

The present invention relates to fragments of SPLUNC1 protein that bind to calcium channels and inhibit calcium influx into airway smooth muscle and other cells. The invention further relates to methods for regulating calcium influx and treating or preventing disorders responsive to modulating calcium influx through calcium channels.

6 Claims, 24 Drawing Sheets

Specification includes a Sequence Listing.

(56) References Cited

OTHER PUBLICATIONS

Curnis "Critical Role of Flanking Residues in NGR-to-isoDGR Transition and CD13/Integrin Receptor Switching" JBC 285(12):9114-9123 (Year: 2010).*
Nguyen "Quantitative mapping of protein-peptide affinity landscapes using spectrally encoded beads" BioRxiv (Year: 2018).*
Main Line Health "Brain Cancer" accessed from mainlinehealth.org on Nov. 19, 2019 (Year: 2019).*
Wikipedia "Calcium Channels" excerpt accessed from wikipedia.org on Nov. 19, 2019 (Year: 2019).*
Brand "Calcium channel blockers ameliorate disease in a mouse model of multiple sclerosis" Exp Neuro 189:5-9 (Year: 2004).*
Wang "Calcium channel blockers may increase risk for pancreatic cancer". accessed from healio.com on Nov. 19, 2019 (Year: 2018).*
International Preliminary Report on Patentability corresponding to International Patent Application No. PCT/US2017/018840 (8 pages) (dated Aug. 28, 2018).
Notification of Transmittal of the International Search Report and the Written Opinion of the International Searching Authority, or the Declaration corresponding to International Application No. PCT/US2017/018840 dated Jun. 8, 2017.
Chen et al. "TRPM7 regulates the migration of human nasopharyngeal carcinoma cell by mediating Ca2+ influx", Cell Calcium 47:425-432 (2010).
Chen et al. "SPLUNC Regulates Cell Progression and Apoptosis through the miR-141-PTEN/p27 Pathway, but is Hindered by LMP1", PLOS One 8(3):e56929 (2013) 12 pages.
Hobbs et al. "Identification of the SPLUNC1 ENaC-inhibitory domain yields novel strategies to treat sodium hyperabsorption in cystic fibrosis airway epithelial cultures", Am J Physiol Lung Cell Mol Physiol 305:L990-L1001 (2013).
Ou et al, "SPLUNC1 reduces the inflammatory response of nasopharyngeal carcinoma cells infected with the EB virus by inhibiting the TLR9/NF-κB pathway", Oncology Reports 33:2779-2788 (2015).
Thaikoottathil et al. "SPLUNC1 Deficiency Enhances Airway Eosinophilic Inflammation in Mice", Am J Respir Cell Mol Biol 47(2):253-260 (2012).
Chu et al. "Function and Regulation of SPLUNC1 Protein in Mycoplasma Infection and Allergic Inflammation", J Immunol 179(6):3995-4002 (2007).
Britto et al. "Bactericidal/Permeability-Increasing Protein Fold-Containing Family Member A1 in Airway Host Protection and Respiratory Disease" American Journal of Respiratory Cell and Molecular Biology, 52(5):525-534 (2015).
Cox et al. "Antibody-Mediated Targeting of the Orail Calcium Channel Inhibits T Cell Function" PLoS ONE, 8(12): e82944 (2013).
Extended European Search Report corresponding to European Patent Application No. 17757105.6 (12 pages) (dated Oct. 9, 2019).
"Human digestive system antigen SEQ ID No. 1561" GENESEQ Database, Accession No. AAM92212 (3 pages) (Nov. 5, 2001).
"Human LunX protein construct, SEQ ID 3" GENESEQ Database, Accession No. BAT04745 (1 page) (Oct. 24, 2013).
Peel et al. "ORAI and Store-Operated Calcium Influx in Human Airway Smooth Muscle Cells" American Journal of Respiratory Cell and Molecular Biology, 38:744-749 (2008).
Wu et al. "Identification of BPIFA1/SPLUNC1as an epithelium-derived smooth muscle relaxing factor" Nature Communications, 8(1):1-10 (2017).
Zhou et al. "Effect of SPLUNC1 protein on the Pseudomonas aeruginosa and Epstein-Barr virus" Molecular and Cellular Biochemistry, 309:191-197 (2008).
Communication pursuant to Article 94(3) EPC corresponding to European Patent Application No. 17757105.6 (7 pages) (dated Nov. 11, 2020).
Database Geneseq [Online] Sep. 7, 2006, "Human PKA-AKAP decoupling peptide No. 610.", retrieved from EBI accession No. GSP:AEI78453, XP 055746820.

* cited by examiner

SEQUENCE LISTING

```
<160> NUMBER OF SEQ ID NOS: 3

<210> SEQ ID NO 1
<211> LENGTH: 256
<212> TYPE: PRT
<213> ORGANISM: Homo sapiens

<400> SEQUENCE: 1

Met Phe Gln Thr Gly Gly Leu Ile Val Phe Tyr Gly Leu Leu Ala Gln
1               5                   10                  15

Thr Met Ala Gln Phe Gly Gly Leu Pro Val Pro Leu Asp Gln Thr Leu
            20                  25                  30
```

```
Pro Leu Asn Val Asn Pro Ala Leu Pro Leu Ser Pro Thr Gly Leu Ala
        35                  40                  45

Gly Ser Leu Thr Asn Ala Leu Ser Asn Gly Leu Leu Ser Gly Gly Leu
 50                  55                  60

Leu Gly Ile Leu Glu Asn Leu Pro Leu Leu Asp Ile Leu Lys Pro Gly
 65                  70                  75                  80

Gly Gly Thr Ser Gly Leu Leu Gly Gly Leu Leu Gly Lys Val Thr
                85                  90                  95

Ser Val Ile Pro Gly Leu Asn Asn Ile Ile Asp Ile Lys Val Thr Asp
            100                 105                 110

Pro Gln Leu Leu Glu Leu Gly Leu Val Gln Ser Pro Asp Gly His Arg
        115                 120                 125

Leu Tyr Val Thr Ile Pro Leu Gly Ile Lys Leu Gln Val Asn Thr Pro
        130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                165                 170                 175

Leu Gly Asp Cys Thr His Ser Pro Gly Ser Leu Gln Ile Ser Leu Leu
                180                 185                 190

Asp Gly Leu Gly Pro Leu Pro Ile Gln Gly Leu Leu Asp Ser Leu Thr
            195                 200                 205

Gly Ile Leu Asn Lys Val Leu Pro Glu Leu Val Gln Gly Asn Val Cys
        210                 215                 220

Pro Leu Val Asn Glu Val Leu Arg Gly Leu Asp Ile Thr Leu Val His
225                 230                 235                 240

Asp Ile Val Asn Met Leu Ile His Gly Leu Gln Phe Val Ile Lys Val
                245                 250                 255

<210> SEQ ID NO 2
<211> LENGTH: 22
<212> TYPE: PRT
<213> ORGANISM: Homo sapiens

<400> SEQUENCE: 2

Asp Ile Thr Leu Val His Asp Ile Val Asn Met Leu Ile His Gly Leu
1               5                   10                  15

Gln Phe Val Ile Lys Val
            20

<210> SEQ ID NO 3
<211> LENGTH: 15
<212> TYPE: PRT
<213> ORGANISM: Homo sapiens

<400> SEQUENCE: 3

Asp Ile Thr Leu Val His Asp Ile Val Asn Met Leu Ile His Gly
1               5                   10                  15
```

PEPTIDE INHIBITORS OF CALCIUM CHANNELS

STATEMENT OF PRIORITY

This application is a 35 U.S.C. 371 national phase application of PCT Application PCT/US2017/018840 filed Feb. 22, 2017 which claims the benefit of U.S. Provisional Application Ser. No. 62/298,204, filed Feb. 22, 2016, the entire contents of each of which are incorporated by reference herein in its entirety.

STATEMENT REGARDING ELECTRONIC FILING OF A SEQUENCE LISTING

A Sequence Listing in ASCII text format, submitted under 37 C.F.R. § 1.821, entitled 5470-775_ST25.txt, 3,053 bytes in size, generated on Aug. 9, 2018 and filed via EFS-Web, is provided in lieu of a paper copy. This Sequence Listing is hereby incorporated by reference into the specification for its disclosures.

FIELD OF THE INVENTION

The present invention relates to fragments of SPLUNC1 protein that bind to calcium channels and inhibit calcium influx into airway smooth muscle and other cells. The invention further relates to methods for regulating calcium influx and treating or preventing disorders responsive to modulating calcium influx through calcium channels.

BACKGROUND OF THE INVENTION

In airway smooth muscle (ASM), the degree of contraction is directly proportional to the cytosolic $Ca^{2+}$ concentration (Janssen, *Canadian Respiratory J.* 5:491 (1998); Roux et al., *Gen. Pharmacol.* 31:349 (1998); Rodger, *Br. Med. Bull.* 48:97 (1992)). As such, ASM $Ca^{2+}$ homeostasis is tightly regulated and often involves store operated $Ca^{2+}$ release (SOCE), a process where stromal interacting molecule 1 (STIM1) relocates/aggregates at the sarcoplasmic reticulum (SR)-plasma membrane junction where it activates calcium release-activated calcium channel protein 1 (Orai 1) to allow $Ca^{2+}$ influx leading to increased contraction (Peel et al., *Am. J Respiratory Cell Mol. Biol.* 38:744 (2008); Suganuma et al., *PloS One* 7:e45056 (2012); Gao et al., *Pulmonary Pharmacol. Ther.* 23:182 (2010)). SOCE is defective in ASM and other cells from asthma patients and in murine asthma models, which show increased Orai1 activity (Spinelli et al., *Pflugers Archie.: Eur. J. Physiol.* 464:481 (2012); Gao et al., *J. Asthma* 50:439 (2013)). The existence of an epithelial-derived smooth muscle relaxing factor (EDSMRF) has been hypothesized since researchers first demonstrated that trachea denuded of epithelia showed airway hyperresponsiveness and that placing epithelia from another animal in the same organ bath reduced contractility (Asano et al., *Int. Arch. Allergy Immunol.* 103:88 (1994); Hay et al., *Eur. J. Pharmacol.* 136:247 (1987)). Candidate molecules, for EDSMRF have included NO, arachidonic acid metabolites, and cytokines, but all have been ultimately rejected since they are not secreted directly into the media nor rapidly modulated by inflammatory mediators, two necessary criteria (Vanhoutte, *Am. J. Physiol. Cell Physiol.* 304:C813 (2013); Tarran et al., *Int. J. Biochem. Cell Biol.* 52:130 (2014)).

Short palate, lung and nasal epithelium clone 1 (SPLUNC1) utilizes its N-terminal S18 region to regulate epithelial $Na^+$ channel (ENaC) plasma membrane density (Hobbs et al., *Am. J. Physiol. Lung Cell. Mol. Physiol.* 305:L990 (2013)). SPLUNC1 production has previously been shown to be inhibited by Th2-type cytokines such as IL-13 that are upregulated in asthma, and in allergic mouse models (Chu et al., *J. Immunol.* 179:3995 (2007)). However, its effects on airway smooth muscle in asthma have not been described.

The present invention addresses previous shortcomings in the art by disclosing the regulation of calcium channels by SPLUNC1 protein fragments and the manipulation of this pathway to regulate calcium influx and smooth muscle contraction and treat disorders responsive to modulating calcium influx.

SUMMARY OF THE INVENTION

The present invention is based, in part, on the discovery of the ability of fragments of SPLUNC1 protein to regulate the activity of calcium channels and through that activity the contractility and reactivity of airway smooth muscle. Additionally, regulation of the activity of calcium channels may be used to inhibit the immune response and inflammation in a subject as well as inhibit cancer cell division. Accordingly, in one aspect the invention relates to a polypeptide consisting essentially of the calcium channel binding domain of a SPLUNC1 protein, or a functional fragment or homolog thereof. In one embodiment, the calcium channel is Orai1. The invention further relates to compositions, e.g., pharmaceutical compositions, and dosage delivery devices comprising the polypeptide or a functional fragment or homolog thereof of the invention.

A further aspect of the invention relates to polynucleotides encoding the polypeptide or a functional fragment or homolog thereof of the invention and vectors and cells comprising the polynucleotide.

An additional aspect of the invention relates to a kit comprising the polypeptide or a functional fragment or homolog thereof and/or composition of the invention.

Another aspect of the invention relates to a method of inhibiting calcium influx through a calcium channel, comprising contacting the calcium channel with the polypeptide or a functional fragment or homolog thereof of the invention, thereby inhibiting calcium influx through the calcium channel.

A further aspect of the invention relates to a method of inhibiting airway smooth muscle contraction, comprising contacting the airway with the polypeptide or a functional fragment or homolog thereof of the invention, thereby inhibiting airway smooth muscle contraction.

An additional aspect of the invention relates to a method of inhibiting airway hyperreactivity, comprising contacting the airway with the polypeptide or a functional fragment or homolog thereof of the invention, thereby inhibiting airway hyperreactivity.

Another aspect of the invention relates to a method of inhibiting an immune response in a subject, comprising delivering to the subject the polypeptide or a functional fragment or homolog thereof of the invention, thereby inhibiting the immune response.

An additional aspect of the invention relates to a method of inhibiting inflammation in a subject, comprising delivering to the subject the polypeptide or a functional fragment or homolog thereof of the invention, thereby inhibiting the inflammation.

A further aspect of the invention relates to a method of treating or preventing an autoimmune disease associated with a calcium channel in a subject in need thereof, comprising contacting the subject with a therapeutically effective amount of the polypeptide or a functional fragment or homolog thereof of the invention, thereby treating or preventing the autoimmune disease.

Another aspect of the invention relates to a method of treating or preventing a cancer associated with a calcium channel in a subject in need thereof, comprising contacting the subject with a therapeutically effective amount of the polypeptide or a functional fragment or homolog thereof of the invention, thereby treating or preventing the cancer.

Another aspect of the invention relates to a method of treating or preventing a disorder responsive to inhibition of calcium influx in an airway in a subject in need thereof, comprising delivering to the subject a therapeutically effective amount of the polypeptide or a functional fragment or homolog thereof or pharmaceutical composition of the invention, thereby treating or preventing the disorder.

A further aspect of the invention relates to the use of a polypeptide or a functional fragment or homolog thereof of the invention in a method of treating or preventing a disorder responsive to inhibition of calcium influx in an airway in a subject in need thereof.

An additional aspect of the invention relates to the use of a polypeptide or a functional fragment or homolog thereof of the invention for the preparation of a medicament to treat or prevent a disorder responsive to inhibition of calcium influx in an airway in a subject in need thereof.

These and other aspects of the invention are set forth in more detail in the description of the invention below.

Human ASMCs were transfected with control and Orai1 shRNA respectively, for 72 h. Fura-2 emission ratio was then recorded over time. (H) Summary of peak fluorescent ratio change in the presence of TG (n=3/group). * Indicates P<0.05,  indicates P<0.01, * indicates P<0.001.

Figure 8:
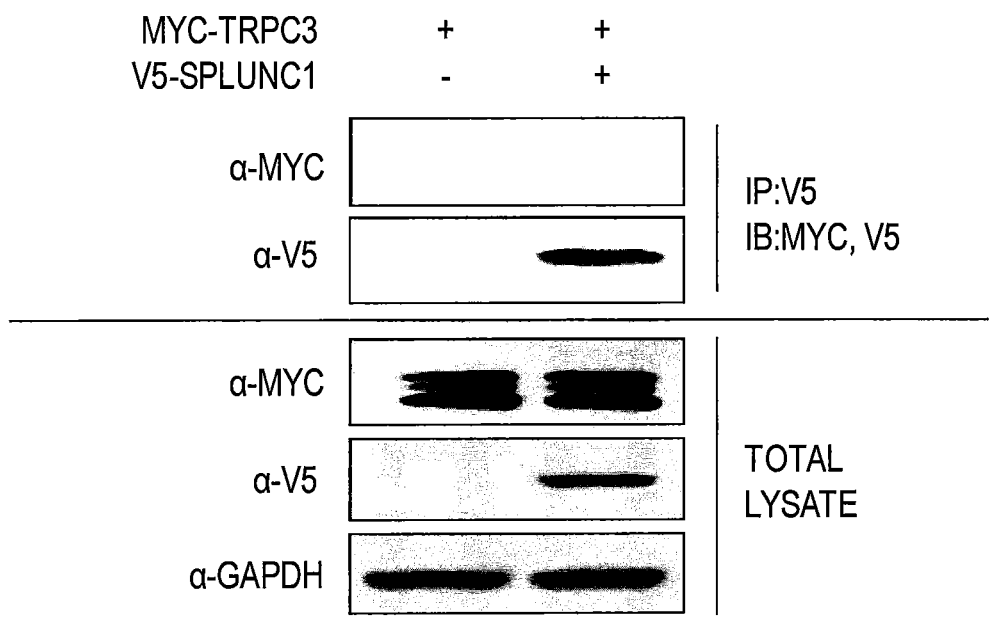

FIG. 8 shows SPLUNC1 does not interact with TRPC3. Immunoprecipitation analysis was performed using cell lysates from HEK293T cells cotransfected with V5-SPLUNC1 and Myc-TRPC3. Data represents an n=3 blots.

Figure 9A:
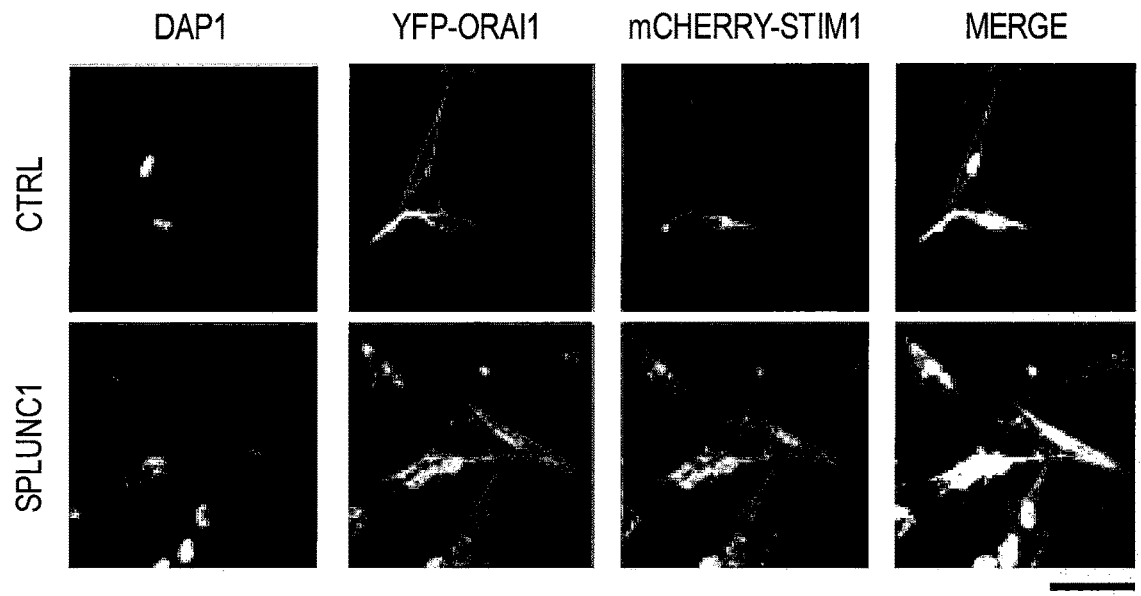
Figure 9B:
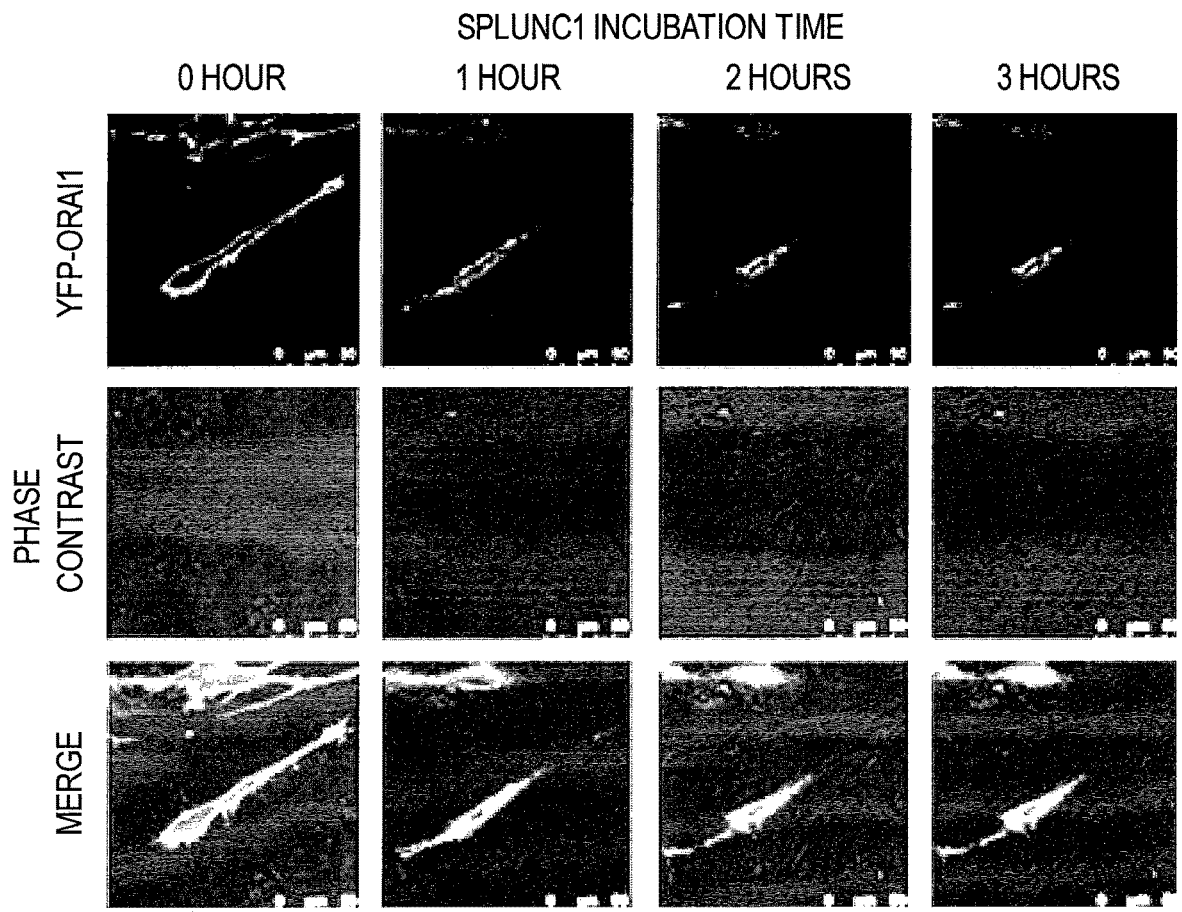

FIGS. 9A-9B show Orai1 is internalized after treated with SPLUNC1. (A) The cellular localization of Orai1 in the presence or absence of SPLUNC1 was detected by confocal microscopy. (B) Time course of YFP-Orai1 internalization in the presence of SPLUNC1. Scale bar in both figures indicates 50 µm.

Figure 10:
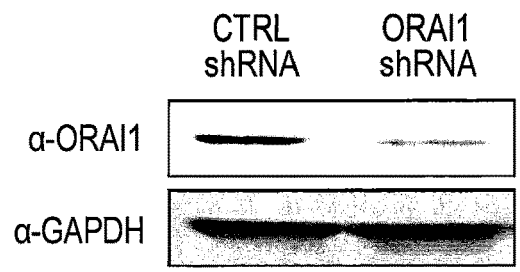

FIG. 10 shows Orai1 is knocked down at the protein level. Representative immunoblots showing Orai1 shRNA decreases Orai1 protein expression in human ASMCs.

Figure 11A:
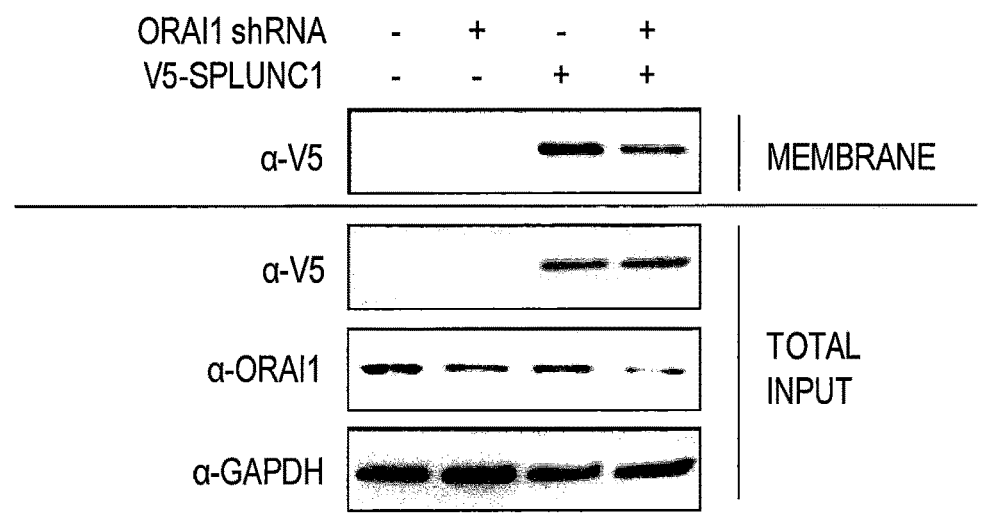
Figure 11B:
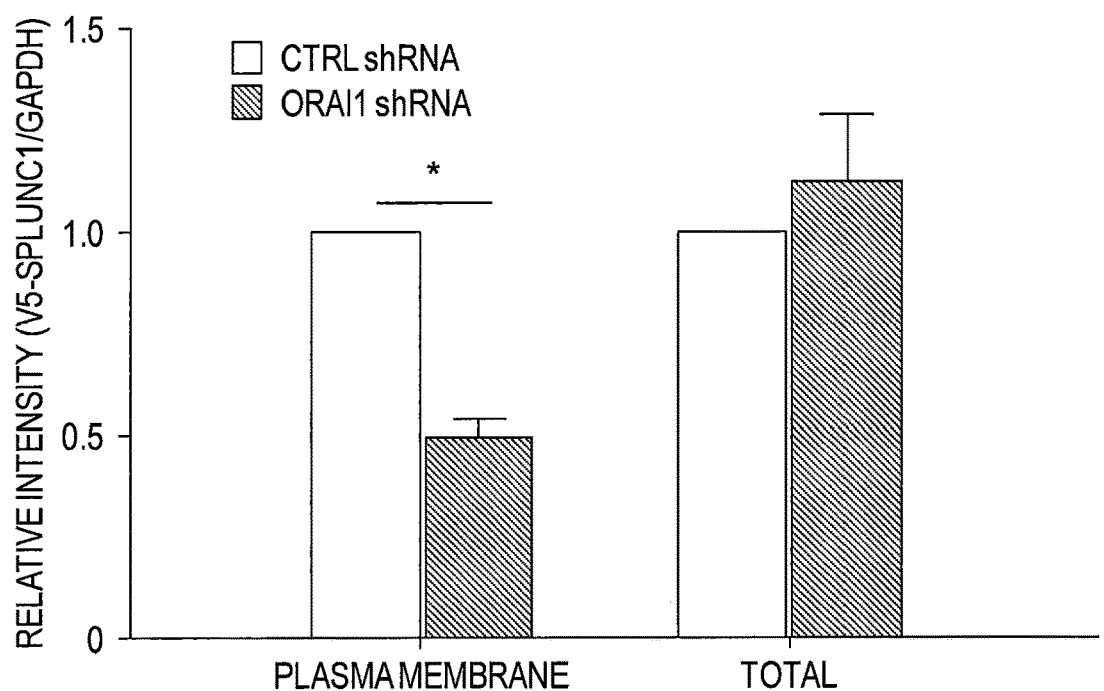

FIGS. 11A-11B show knock down of Orai1 using shRNA decreases SPLUNC1 binding to the ASMC membrane. (A) Human ASMCs were transfected with scrambled control and Orai1 shRNA respectively for 72 h. Cells were incubated in the presence or absence of SPLUNC1, followed by surface biotinylation and immunoblot using indicated antibodies. (B) Intensity of immunoblots from (A) were quantified using Image J, normalized to GAPDH and expressed as relative intensity (n=3). * Indicates P<0.05.

Figure 12A:
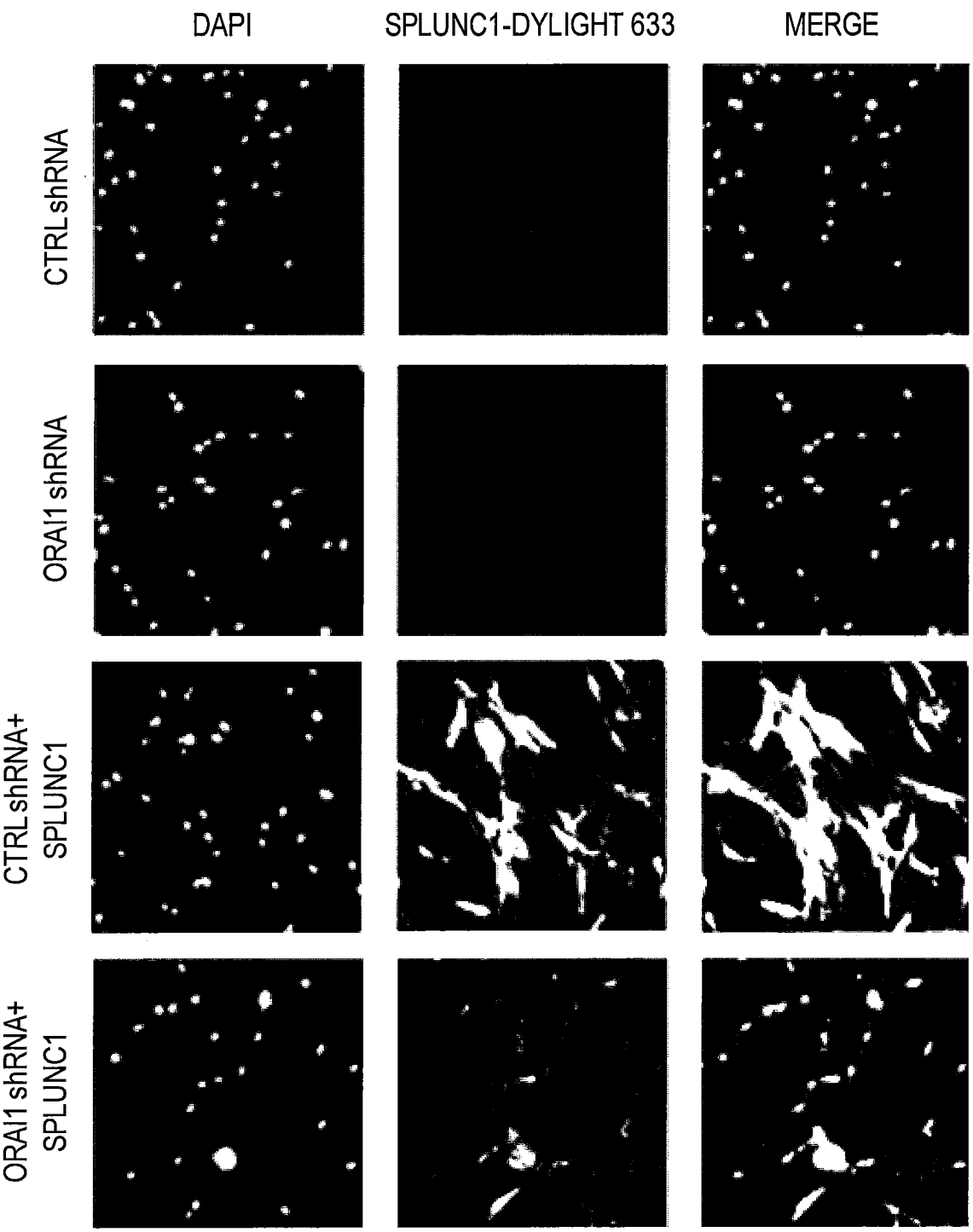
Figure 12B:
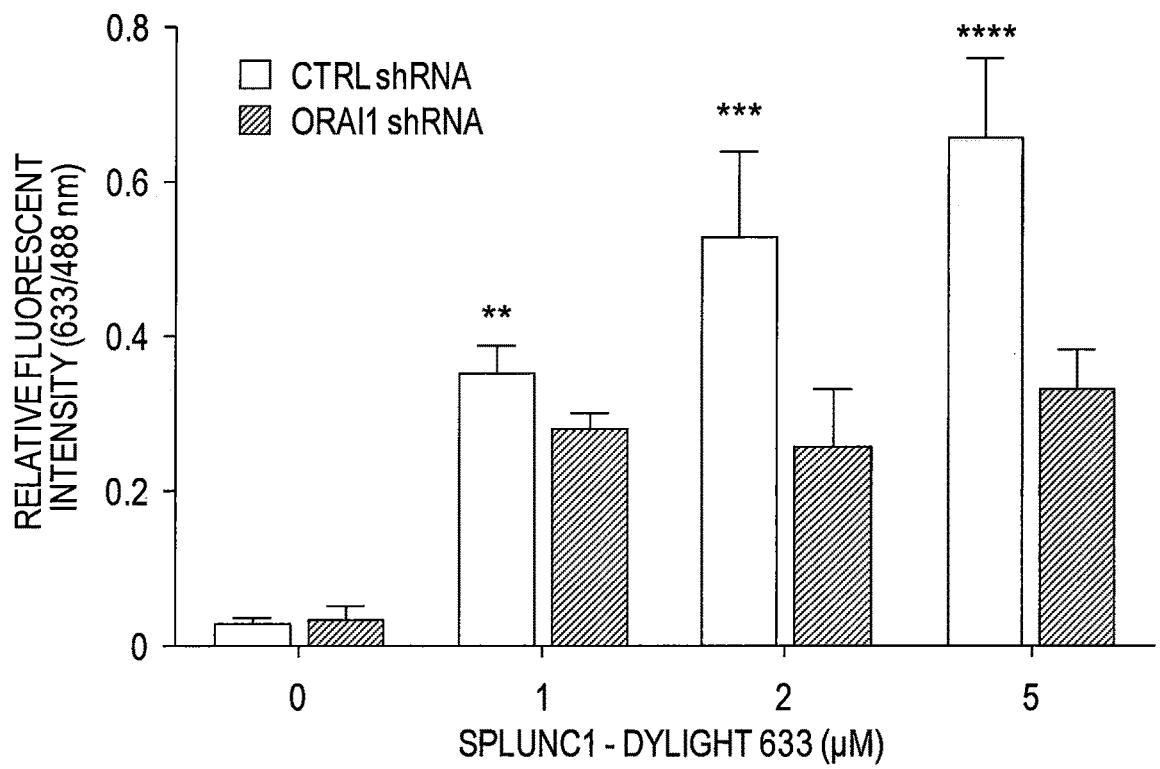

FIGS. 12A-12B show knock down of Orai1 decreases fluorescent SPLUNC1 binding to ASMCs. (A) SPLUNC1 was labeled with DyLight-633. Human ASMCs were transfected with scrambled control shRNA and Orai1 shRNA respectively. 72 h post transfection, cells were treated with or without SPLUNC1-DyLight 633 for 1 h, then washed for 5 times with ice-cold Ringer's solution. Fluorescent images were taken using Leica SP8. Scale bar indicates 75 µm. (B) ASMCs bounded SPLUNC1-Dylight 633 was detected by fluorescent plate reader. Cells were also stained with calcein as cell number control. Relative fluorescent intensity was calculated by normalizing Dylight 633 to calcein.

Figure 13:
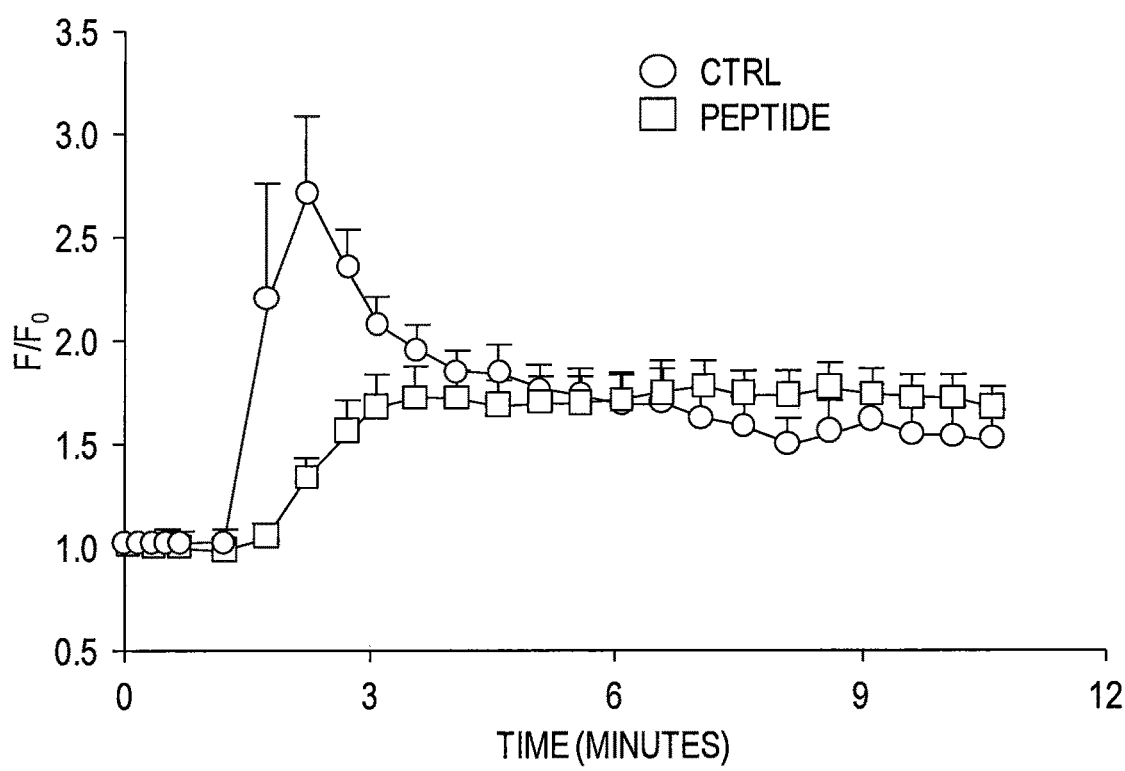

FIG. 13 shows SPLUNC1 derived peptide inhibits thapsigargin-induced $Ca^{2+}$ release in human airway smooth muscle. ASM were loaded with Fura2-AM and the change in fluorescence (F340/F380) was measured Over time as an indicator the change in cytosolic $Ca^{2+}$ using epifluorescent microscopy. All n=3.

Figure 14:
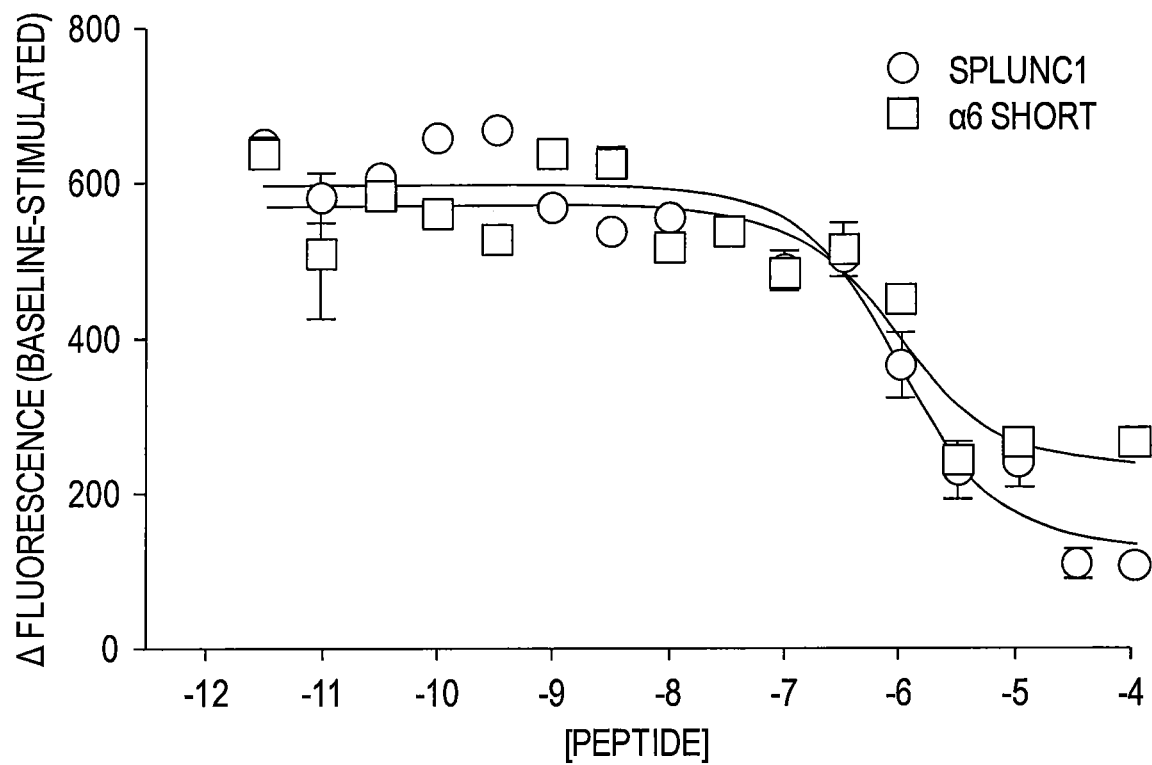
Figure 14:
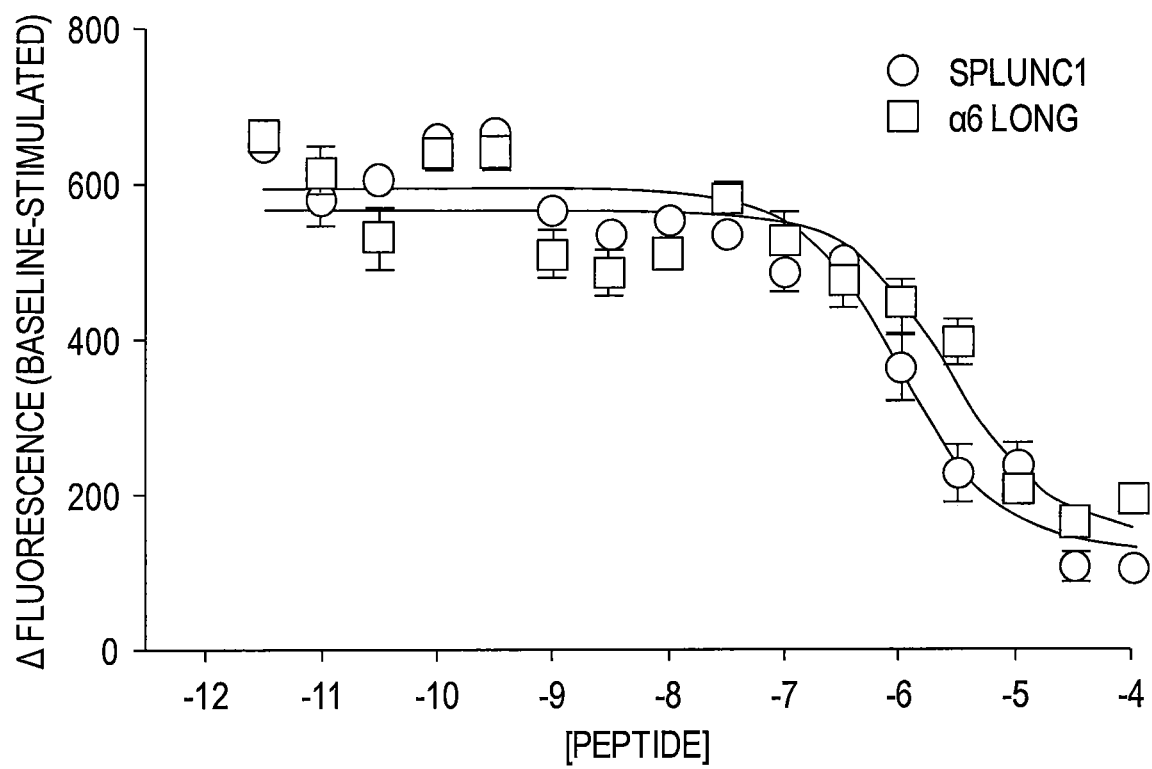

FIG. 14 shows α6 peptides inhibit thapsigargin-induced $Ca^{2+}$ signaling in HEK293T cells. HEK293T cells, cultured in 384 well plates were loaded with Fluo4 and the change in fluorescence was obtained using a Tecan plate reader. Full dose responses were obtained for full length SPLUNC1 and the short and long α6 peptides. All experiments were performed on 3 separate occasions.

Figure 15:
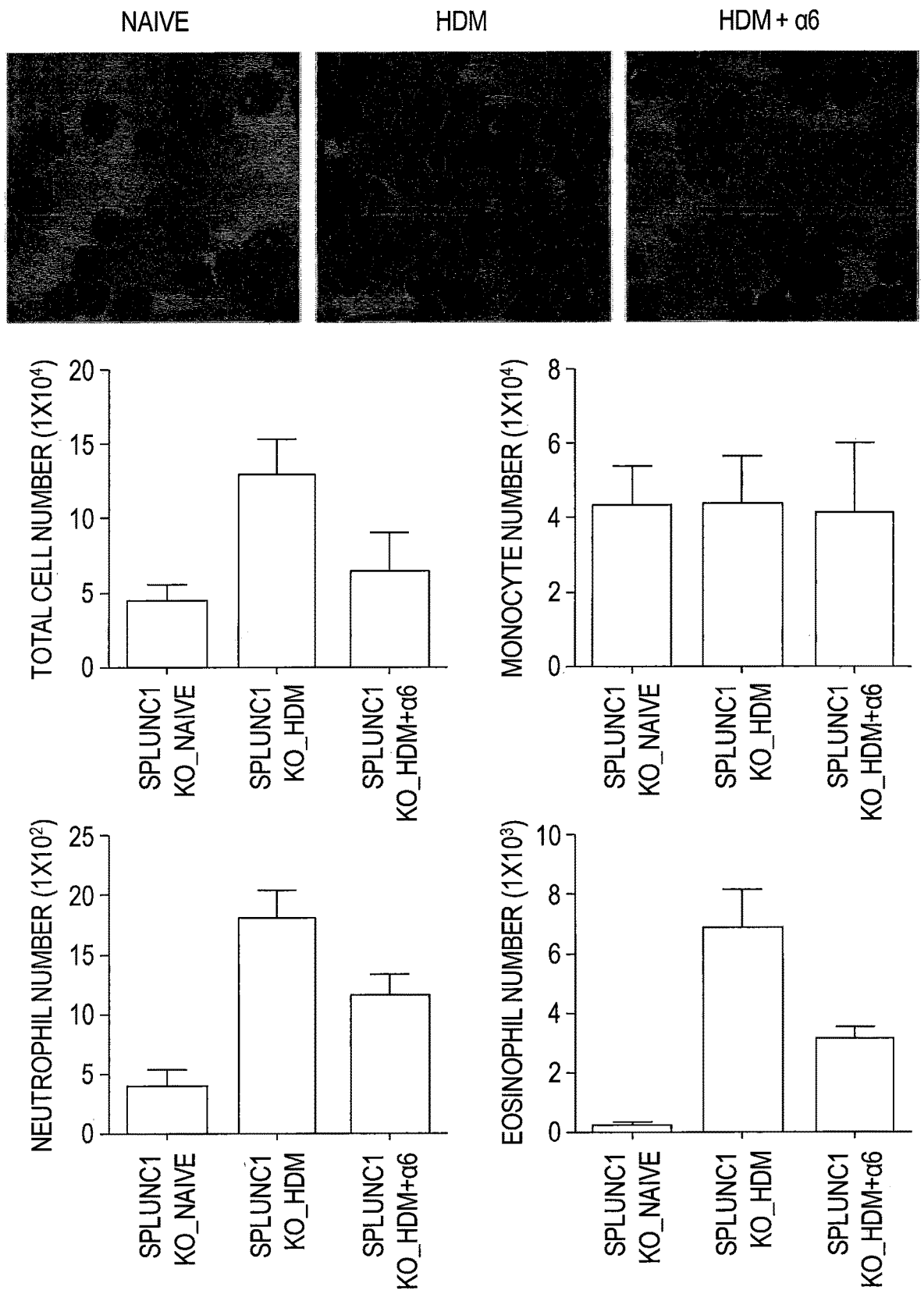

FIG. 15 shows inhaled α6 peptides reduce inflammatory cell counts in the lungs of an allergic mouse model. SPLUNC1$^{-/-}$ knockout mice were first sensitized with 2 µg of house dust mite extract (HDM) intranasally on day 0 and day 14. After this time, they were then challenged with 20 µg HDM intranasally from day 14-day 17. Some mice were treated with 320 µM α6 peptide in PBS on day 15 and day 16. Broncho-alveolar lavage was obtained and differential cell counts were performed. Bar graphs show the results of total cell counts and for individual cell populations as specified under control (naïve), house dust mite (HDM) and HDM/α6 peptide conditions.

Figure 16:
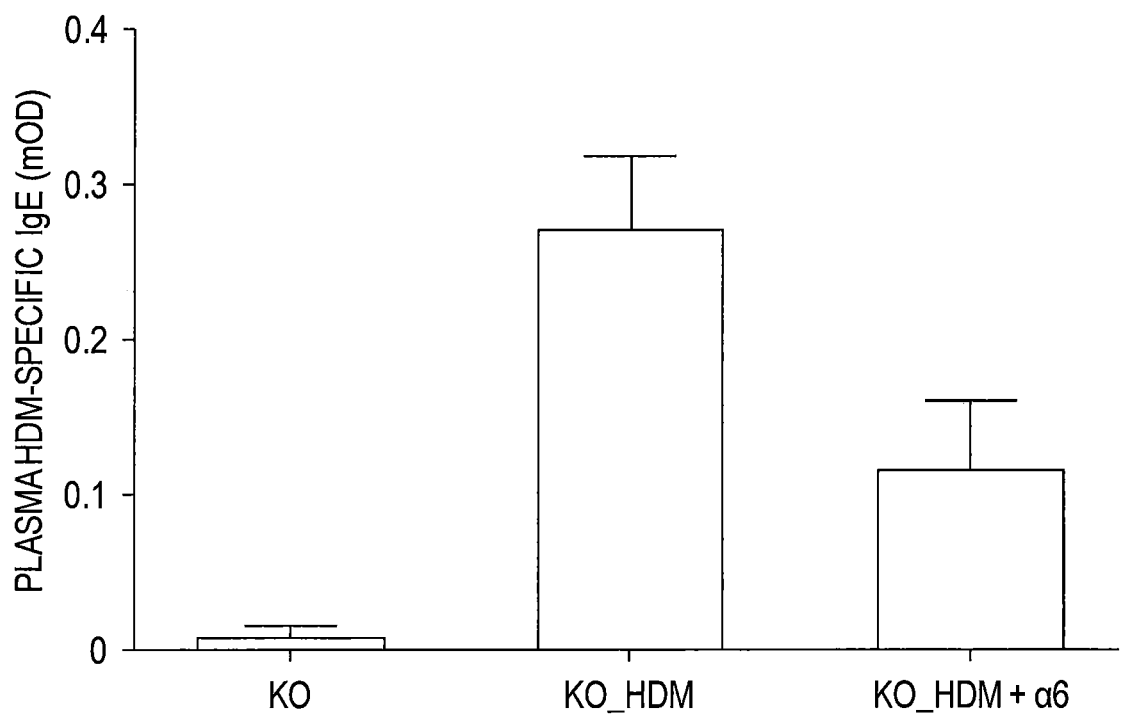

FIG. 16 shows inhaled α6 peptides reduce blood IgE levels in an allergic mouse model. SPLUNC1$^{-/-}$ knockout mice were first sensitized with 2 µg of house dust mite extract (HDM) intranasally on day 0 and day 14. After this time, they were then challenged with 20 µg HDM intranasally on days 14-17. Some mice were treated with 320 µM α6 peptide in PBS on day 15 and day 16. Serum was then taken and HDM-specific IgE levels were measured by ELISA.

DETAILED DESCRIPTION OF THE INVENTION

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety.

Amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

The term "consists essentially of" (and grammatical variants), as applied to a peptide sequence of this invention, means a peptide that consists of both the recited sequence (e.g., SEQ ID NO) and a total of ten or less (e.g., 1, 2, 3, 4, 5, 6, 7, 8, 9, or 10) additional amino acids on the N-terminal and/or C-terminal ends of the recited sequence such that the function of the peptide is not materially altered. The total of ten or less additional amino acids includes the total number of additional amino acids on both ends added together. The term "materially altered," as applied to peptides of the invention, refers to an increase or decrease in binding activity (e.g., to a calcium channel) of at least about 50% or more as compared to the activity of a peptide consisting of the recited sequence.

The term "modulate," "modulates," or "modulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

The term "contact" or grammatical variations thereof as used with respect to a polypeptide and a calcium channel, refers to bringing the polypeptide and the calcium channel in sufficiently close proximity to each other for one to exert a biological effect on the other. In some embodiments, the term contact means binding of the polypeptide to the calcium channel.

By the terms "treat," "treating," or "treatment of," it is intended that the severity of the subject's condition is reduced or at least partially improved or modified and that some alleviation, mitigation or decrease in at least one clinical symptom is achieved.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

A "prophylactically effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The term "fragment," as applied to a peptide, will be understood to mean an amino acid sequence of reduced length relative to a reference peptide or amino acid sequence and comprising, consisting essentially of, and/or consisting of an amino acid sequence of contiguous amino acids identical to the reference peptide or amino acid sequence. Such a peptide fragment according to the invention may be, where appropriate, included in a larger polypeptide of which it is a constituent. In some embodiments, such fragments can comprise, consist essentially of, and/or consist of peptides having a length of at least about 4, 5, 6, 7, 8, 9, 10, 11, 12, 13, 14, 15 or more consecutive amino acids of a peptide or amino acid sequence according to the invention. In other embodiments, such fragments can comprise, consist essentially of, and/or consist of peptides having a length of less than about 15, 14, 13, 12, 11, 10, 9, 8, 7, 6, 5, 4, or less consecutive amino acids of a peptide or amino acid sequence according to the invention.

As used herein, the terms "protein" and "polypeptide" are used interchangeably and encompass both peptides and proteins, unless indicated otherwise.

The "N-terminus" of a polypeptide is any portion of the polypeptide that starts from the N-terminal amino acid residue and continues to a maximum of the midpoint of the polypeptide.

The "C-terminus" of a polypeptide is any portion of the polypeptide that starts from the C-terminal amino acid residue and continues to a maximum of the midpoint of the polypeptide.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a peptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" peptide or "functional fragment" is one that substantially retains at least one biological activity normally associated with that peptide (e.g., binding to or inhibiting a calcium channel). In particular embodiments, the "functional" peptide or "functional fragment" substantially retains all of the activities possessed by the unmodified peptide. By "substantially retains" biological activity, it is meant that the peptide retains at least about 50%, 60%, 75%, 85%, 90%, 95%, 97%, 98%, 99%, or more, of the biological activity of the native polypeptide (and can even have a higher level of activity than the native peptide). A "non-functional" peptide is one that exhibits little or essentially no detectable biological activity normally associated with the peptide (e.g., at most, only an insignificant amount, e.g., less than about 10% or even 5%). Biological activities such as protein binding and calcium channel inhibitory activity can be measured using assays that are well known in the art and as described herein.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid or nucleotide sequence of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

An isolated cell refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al, Canadian Patent Application No. 2,012,311, filed Mar. 15, 1990).

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931).

It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

The term "transfection" or "transduction" means the uptake of exogenous or heterologous nucleic acid (RNA and/or DNA) by a cell. A cell has been "transfected" or "transduced" with an exogenous or heterologous nucleic acid when such nucleic acid has been introduced or delivered inside the cell. A cell has been "transformed" by exogenous or heterologous nucleic acid when the transfected or transduced nucleic acid imparts a phenotypic change in the cell and/or a change in an activity or function of the cell. The transforming nucleic acid can be integrated (covalently linked) into chromosomal DNA making up the genome of the cell or it can be present as a stable plasmid.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

A first aspect of the invention relates to products that can be used to carry out the methods disclosed herein. Thus, one aspect of the invention relates to a polypeptide comprising, consisting essentially of, or consisting of the calcium channel binding domain of a SPLUNC1 protein, or a functional fragment or homolog thereof. In some embodiments, the calcium channel is Orai1, e.g., human Orai1. In some embodiments, the polypeptide is a functional fragment of human SPLUNC1 protein or a homolog thereof.

In exemplary embodiments, the polypeptide is a fragment of SPLUNC1 comprising, consisting essentially of, or consisting of the calcium channel binding domain. In some embodiments, the fragment of the SPLUNC1 protein comprises, consists essentially of, or consists of the publicly known amino acid sequence of the SPLUNC1 protein (e.g., as disclosed in GenBank and disclosed herein). In another embodiment, the fragment of the SPLUNC1 protein comprises, consists essentially of, or consists of an amino acid sequence that is at least 70% identical, e.g., at least 75%, 80%, 85%, 90%, 95%, 96%, 97%, 98%, or 99% identical to the publicly known amino acid sequence.

The amino acid sequence of human SPLUNC1 (SEQ ID NO:1) is disclosed below. The conserved cysteine residues that are spaced 43 amino acids apart and may be important for activity are indicated.

```
SPLUNC1
         10         20         30         40         50         60
MFQTGGLIVF YGLLAQTMAQ FGGLPVPLDQ TLPLNVNPAL PLSPTGLAGS LTNALSNGLL 70         80         90        100        110        120
SGGLLGILEN LPLLDILKPG GGTSGGLLGG LLGKVTSVIP GLNNIIDIKV TDPQLLELGL 130        140        150        160        170        180
VQSPDGHRLY VTIPLGIKLQ VNTPLVGASL LRLAVKLDIT AEILAVRDKQ ERIHLVLGDC 190        200        210        220        230        240
THSPGSLQIS LLDGLGPLPI QGLLDSLTGI LNKVLPELVQ GNVCPLVNEV LRGLDITLVH

250
DIVNMLIHGL QFVIKV
```

The polypeptide of the invention also includes functional portions or fragments of the calcium channel binding domain of SPLUNC1. The length of the fragment is not critical as long as it substantially retains the biological activity of the polypeptide (e.g., calcium channel binding activity). Illustrative fragments comprise at least about 4, 6, 8, 10, 12, 15, 20, 25, 30, 35, 40, 45, 50, 75, 100, 150, 200, or more contiguous amino acids of a SPLUNC1 protein. In other embodiments, the fragment comprises no more than about 200, 150, 100, 75, 50, 45, 40, 35, 30, 25, 20, 15, 12, 10, 8, 6, or 4 contiguous amino acids of a SPLUNC1 protein. In certain embodiments, the fragment is about 5 to about 30 amino acids, about 5 to about 25 amino acids, about 5 to about 20 amino acids, about 10 to about 30 amino acids, about 10 to about 25 amino acids, about 10 to about 20 amino acids, about 15 to about 30 amino acids, about 15 to about 25 amino acids, or about 15 to about 20 amino acids.

In one embodiment, the fragment comprises, consists essentially of, or consists of the C-terminus of SPLUNC1, e.g., the C-terminal 100 amino acid residues or less, e.g., the C-terminal 100, 90, 80, 70, 60, 50, 45, 40, 35, 30, 25, 20, 15, 10 or less amino acid residues.

In one embodiment, the functional fragment comprises, consists essentially of, or consists of the amino acid sequence DITLVHDIVNMLIHGLQFVIKV (SEQ ID NO:2), corresponding to amino acids 235-256 of human SPLUNC1, or an amino acid sequence that has at least 70% sequence identity thereto, e.g., at least 75%, 80%, 85%, 90%, 95%, 96%, 97%, 98%, or 99% sequence identity thereto, or a functional fragment or homolog thereof. In other embodiments, the functional fragment comprises, consists essentially of, or consists of the amino acid sequence DITLVHDIVNMLIHG (SEQ ID NO:3), corresponding to amino acids 235-249 of human SPLUNC1, or an amino acid sequence that has at least 70% sequence identity thereto, e.g., at least 75%, 80%, 85%, 90%, 95%, 96%, 97%, 98%, or 99% sequence identity thereto, or a functional fragment or homolog thereof.

Likewise, those skilled in the art will appreciate that the present invention also encompasses fusion polypeptides (and polynucleotide sequences encoding the same) comprising a fragment of a SPLUNC1 protein. For example, it may be useful to express the polypeptide (or functional fragment) as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the polypeptide may be produced, e.g., fusion proteins comprising maltose binding protein (MBP) or glutathione-S-transferase. As another alternative, the fusion protein can comprise a reporter molecule. In other embodiments, the fusion protein can comprise a polypeptide that provides a function or activity that is the same as or different from the activity of the polypeptide, e.g., a targeting, binding, or enzymatic activity or function.

Likewise, it will be understood that the polypeptides specifically disclosed herein will typically tolerate substitutions (e.g., conservative substitutions) in the amino acid sequence and substantially retain biological activity. To identify polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to the following codon table:

TABLE 1

| Amino Acid | | | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |

TABLE 1-continued

| Amino Acid | | | Codons |
|---|---|---|---|
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

In identifying amino acid sequences encoding polypeptides other than those specifically disclosed herein, the hydropathic index of amino acids may be considered. The importance of the hydropathic amino acid index in conferring interactive biologic function on a protein is generally understood in the art (see, Kyte and Doolittle, *J. Mol. Biol.* 157:105 (1982); incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, id.), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±l); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional polypeptides beyond those specifically disclosed herein.

As used herein, the term "homolog" is used to refer to a molecule which differs from a naturally occurring polypeptide by minor modifications to the naturally occurring polypeptide, but which significantly retains a biological activity of the naturally occurring polypeptide. Minor modifications include, without limitation, changes in one or a few amino acid side chains, changes to one or a few amino acids (including deletions, insertions, and/or substitutions), changes in stereochemistry of one or a few atoms, and minor derivatizations, including, without limitation, methylation, glycosylation, phosphorylation, acetylation, myristoylation, prenylation, palmitoylation, amidation, and addition of glycosylphosphatidyl inositol. The term "substantially retains," as used herein, refers to a fragment, homolog, or other variant of a polypeptide that retains at least about 50% of the activity of the naturally occurring polypeptide (e.g., binding to or inhibiting a calcium channel), e.g., about 70%, 80%, 90% or more. Other biological activities, depending on the polypeptide, may include pH sensitivity, enzyme activity, receptor binding, ligand binding, induction of a growth factor, a cell signal transduction event, etc.

In certain embodiments, the polypeptide of the invention comprises at least one modified terminus, e.g., to protect the polypeptide against degradation. In some embodiments, the N-terminus is acetylated and/or the C-terminus is amidated. In some embodiments, the polypeptide comprises one or two D-alanines at the amino- and/or carboxyl-terminal ends.

In certain embodiments, the polypeptide of the invention comprises at least one non-natural amino acid (e.g., 1, 2, 3, or more) or at least one terminal modification (e.g., 1 or 2). In some embodiments, the peptide comprises at least one non-natural amino acid and at least one terminal modification.

In certain embodiments, the polypeptide mimics the calcium channel binding domain of a SPLUNC1 protein. The calcium channel binding domain is the minimal fragment of the PLUNC protein required to have substantially the same binding activity to the calciumchannel as the full length SPLUNC1 protein. The term "substantially the same binding activity" refers to an activity that is at least about 50% of the binding activity of the full length protein, e.g., at least about 60%, 70%, 80%, or 90% of the binding activity. In some embodiments, the peptide has at least the same binding activity as the full length SPLUNC 1 protein. In one embodiment, the calcium channel is Orai1, e.g., human Orai1. In another embodiment, the calcium channel is one that is similar in sequence and/or structure to Orai1.

One aspect of the invention relates to a polynucleotide encoding the polypeptide of the invention. In embodiments of the invention, the polynucleotide encoding the polypeptide will hybridize to the nucleic acid sequences encoding SPLUNC1 proteins that are known in the art or fragments thereof under standard conditions as known by those skilled in the art and encode a functional polypeptide or functional fragment thereof.

For example, hybridization of such sequences may be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and conditions represented by a wash stringency of 50% formamide with 5×Denhardt's solution, 0.5% SDS and 1×SSPE at 42° C., respectively) to the polynucleotide sequences encoding the PLUNC protein or functional fragments thereof specifically disclosed herein. See, e.g., Sambrook et al., Molecular Cloning: A Laboratory Manual 2nd Ed. (Cold Spring Harbor, N.Y., 1989).

In other embodiments, polynucleotide sequences encoding the polypeptide have at least about 70%, 80%, 85%, 90%, 95%, 96%, 97%, 98%, 99% or higher sequence identity with the publicly known nucleic acid sequences (disclosed in GenBank) or functional fragments thereof and encode a functional polypeptide or functional fragment thereof.

Further, it will be appreciated by those skilled in the art that there can be variability in the polynucleotides that encode the polypeptides (and fragments thereof) of the present invention due to the degeneracy of the genetic code. The degeneracy of the genetic code, which allows different nucleic acid sequences to code for the same polypeptide, is well known in the literature (See, e.g., Table 1).

As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Those skilled in the art will appreciate that the isolated polynucleotides encoding the polypeptides of the invention will typically be associated with appropriate expression control sequences, e.g., transcription/translation control signals and polyadenylation signals.

It will further be appreciated that a variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the polypeptide coding sequence can be operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter.

Inducible promoter/enhancer elements include hormone-inducible and metal-inducible elements, and other promoters regulated by exogenously supplied compounds, including without limitation, the zinc-inducible metallothionein (MT) promoter; the dexamethasone (Dex)-inducible mouse mammary tumor virus (MMTV) promoter; the T7 polymerase promoter system (see WO 98/10088); the ecdysone insect promoter (No et al., *Proc. Natl. Acad. Sci. USA* 93:3346 (1996)); the tetracycline-repressible system (Gossen et al., *Proc. Natl. Acad. Sci. USA* 89:5547 (1992)); the tetracycline-inducible system (Gossen et al., *Science* 268:1766 (1995); see also Harvey et al., *Curr. Opin. Chem. Biol.* 2:512 (1998)); the RU486-inducible system (Wang et al., *Nat. Biotech.* 15:239 (1997); Wang et a, *Gene Ther.*, 4:432

(1997)); and the rapamycin-inducible system (Magari et al., *J. Clin. Invest.* 100:2865 (1997)).

Moreover, specific initiation signals are generally required for efficient translation of inserted polypeptide coding sequences. These translational control sequences, which can include the ATG initiation codon and adjacent sequences, can be of a variety of origins, both natural and synthetic.

The present invention further provides cells comprising the isolated polynucleotides and polypeptides of the invention. The cell may be a cultured cell or a cell in vivo, e.g., for use in therapeutic methods, diagnostic methods, screening methods, methods for studying the biological action of the SPLUNC1 protein, in methods of producing the polypeptides, or in methods of maintaining or amplifying the polynucleotides of the invention, etc. In another embodiment, the cell is an ex vivo cell that has been isolated from a subject. The ex vivo cell may be modified and then reintroduced into the subject for diagnostic or therapeutic purposes.

In particular embodiments, the cell is an untransformed airway smooth muscle cell or a cell from an airway smooth muscle cell line.

The isolated polynucleotide can be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a polypeptide operatively associated with the promoter, and, optionally, a termination sequence including a stop signal for RNA polymerase and a polyadenylation signal for polyadenylase.

Non-limiting examples of promoters of this invention include CYC1, HIS3, GAL1, GAL4, GAL10, ADH1, PGK, PHO5, GAPDH, ADC1, TRP1, URA3, LEU2, ENO, TPI, and alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, pathogenesis or disease related-promoters, cauliflower mosaic virus 35S, CMV 35S minimal, cassaya vein mosaic virus (CsVMV), chlorophyll a/b binding protein, ribulose 1,5-bisphosphate carboxylase, shoot-specific promoters, root specific promoters, chitinase, stress inducible promoters, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells).

Further examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, baculovirus IE1 promoter, elongation factor 1 alpha (EF1) promoter, phosphoglycerate kinase (PGK) promoter, ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis and/or disease-related promoters, and promoters that exhibit tissue specificity, such as the elastase I gene control region, which is active in pancreatic acinar cells; the insulin gene control region active in pancreatic beta cells, the immunoglobulin gene control region active in lymphoid cells, the mouse mammary tumor virus control region active in testicular, breast, lymphoid and mast cells; the albumin gene promoter, the Apo AI and Apo AII control regions active in liver, the alpha-fetoprotein gene control region active in liver, the alpha 1-antitrypsin gene control region active in the liver, the beta-globin gene control region active in myeloid cells, the myelin basic protein gene control region active in oligodendrocyte cells in the brain, the myosin light chain-2 gene control region active in skeletal muscle, and the gonadotropic releasing hormone gene control region active in the hypothalamus, the pyruvate kinase promoter, the villin promoter, the promoter of the fatty acid binding intestinal protein, the promoter of smooth muscle cell α-actin, and the like. In addition, any of these expression sequences of this invention can be modified by addition of enhancer and/or regulatory sequences and the like.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

It will be apparent to those skilled in the art that any suitable vector can be used to deliver the polynucleotide to a cell or subject. The vector can be delivered to cells in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Suitable vectors include plasmid vectors, viral vectors (e.g., retrovirus, alphavirus; vaccinia virus; adenovirus, adeno-associated virus and other parvoviruses, lentivirus, poxvirus, or herpes simplex virus), lipid vectors, poly-lysine vectors, synthetic polyamino polymer vectors, and the like.

Any viral vector that is known in the art can be used in the present invention. Protocols for producing recombinant viral vectors and for using viral vectors for nucleic acid delivery can be found in Ausubel et al., Current Protocols in Molecular Biology (Green Publishing Associates, Inc. and John Wiley & Sons, Inc., New York) and other standard laboratory manuals (e.g., Vectors for Gene Therapy. In: *Current Protocols in Human Genetics*. John Wiley and Sons, Inc.: 1997).

Non-viral transfer methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, poly-lysine conjugates, and artificial viral envelopes.

In particular embodiments, plasmid vectors are used in the practice of the present invention. For example, naked plasmids can be introduced into muscle cells by injection into the tissue. Expression can extend over many months, although the number of positive cells is typically low (Wolff et al., *Science* 247:247 (1989)). Cationic lipids have been demonstrated to aid in introduction of nucleic acids into some cells in culture (Feigner and Ringold, *Nature* 337:387 (1989)). Injection of cationic lipid plasmid DNA complexes into the circulation of mice has been shown to result in expression of the DNA in lung (Brigham et al., *Am. J. Med. Sci.* 298:278 (1989)). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell surface antigens of the target tissue (Mizuno et al., *No Shinkei Geka* 20:547 (1992); PCT publication WO 91/06309; Japanese patent application 1047381; and European patent publication EP-A-43075).

Liposomes that consist of amphiphilic cationic molecules are useful as non-viral vectors for nucleic acid delivery in vitro and in vivo (reviewed in Crystal, *Science* 270:404 (1995); Blaese et al., *Cancer Gene Ther.* 2:291 (1995); Behr et al., *Bioconjugate Chem.* 5:382 (1994); Remy et al., *Bioconjugate Chem.* 5:647 (1994); and Gao et al., *Gene Therapy* 2:710 (1995)). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Feigner et al., *Proc. Natl. Acad. Sci. USA* 84:7413 (1987); Loeffler et al., *Meth. Enzymol.* 217:599 (1993); Feigner et al., *J. Biol. Chem.* 269:2550 (1994)).

Several groups have reported the use of amphiphilic cationic lipid:nucleic acid complexes for in vivo transfection both in animals and in humans (reviewed in Gao et al., *Gene Therapy* 2:710 (1995); Zhu et al., *Science* 261:209 (1993); and Thierry et al., *Proc. Natl. Acad. Sci. USA* 92:9742 (1995)). U.S. Pat. No. 6,410,049 describes a method of preparing cationic lipid:nucleic acid complexes that have a prolonged shelf life.

Expression vectors can be designed for expression of polypeptides in prokaryotic or eukaryotic cells. For example, polypeptides can be expressed in bacterial cells such as *E. coli*, insect cells (e.g., the baculovirus expression system), yeast cells, plant cells or mammalian cells. Some suitable host cells are discussed further in Goeddel, *Gene Expression Technology*: Methods in Enzymology 185, Academic Press, San Diego, Calif. (1990). Examples of bacterial vectors include pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast *S. cerevisiae* include pYepSec1 (Baldari et al., *EMBO J.* 6:229 (1987)), pMFa (Kurjan and Herskowitz, *Cell* 30:933 (1982)), pJRY88 (Schultz et al., *Gene* 54:113 (1987)), and pYES2 (Invitrogen Corporation, San Diego, Calif.). Baculovirus vectors available for expression of nucleic acids to produce proteins in cultured insect cells (e.g., Sf9 cells) include the pAc series (Smith et al., *Mol. Cell. Biol.* 3:2156 (1983)) and the pVL series (Lucklow and Summers *Virology* 170:31 (1989)).

Examples of mammalian expression vectors include pWLNEO, pSV2CAT, pOG44, pXT1, pSG (Stratagene) pSVK3, PBPV, pMSG, PSVL (Pharmacia), pCDM8 (Seed, *Nature* 329:840 (1987)) and pMT2PC (Kaufman et al., *EMBO J.* 6:187 (1987)). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA and RNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

A further aspect of the invention relates to a composition comprising the polypeptide or a functional fragment or homolog thereof of the invention and a carrier. In some embodiments, the composition is a pharmaceutical composition comprising the polypeptide or a functional fragment or homolog thereof of the invention and a pharmaceutically acceptable carrier.

An additional aspect of the invention relates to a dosage delivery device comprising the pharmaceutical composition. In some embodiments, the dosage delivery device is an inhaler for delivery of the composition to the airways of a subject, e.g., by oral and/or nasal inhalation.

Another aspect of the invention relates to a kit comprising the polypeptide or a functional fragment or homolog thereof of the invention and useful for carrying out the methods of the invention. The kit may further comprise additional reagents for carrying out the methods (e.g., buffers, containers, additional therapeutic agents) as well as instructions.

The methods of the invention relates to the ability of polypeptides to bind to a calcium channel and inhibit calcium influx into a cell comprising the calcium channel. Thus, one aspect of the present invention relates to a method of inhibiting calcium influx through a calcium channel, comprising contacting the calcium channel with the polypeptide of the invention, thereby inhibiting calcium influx through the calcium channel. In some embodiments, the calcium influx is store operated calcium influx. In one embodiment, the calcium channel is Orai1, e.g., human Orai1, or a non-human mammalian Orai1. In another embodiment, the calcium channel is one that is similar in sequence and/or structure to Orai1. The inhibition of calcium channel activity can be measured by any method known in the art or disclosed herein, including, without limitation, measuring calcium flow or change in potential across a membrane, across a cell, or across a natural or artificial lining. The inhibition can be at least about 20%, e.g., at least about 30%, 40%, 50%, 60%, 70%, 80%, 90%, or 100%.

The method of inhibiting the calcium channel can be carried out, e.g., on an isolated calcium channel, a calcium channel in an artificial membrane, or a calcium channel in a cell. In one embodiment, the calcium channel is present in an isolated cell, e.g., a cultured primary cell or cell line. In certain embodiments, the cell is an airway smooth muscle cell, e.g., part of an airway smooth muscle cell culture. In another embodiment, the isolated cell is part of an epithelial cell culture, e.g., a natural or artificial epithelial lining, e.g., a cell culture in a device (such as an Ussing chamber) in which characteristics such as ion flow and/or potential can be measured across a lining. In another embodiment, the isolated cell is an immune system cell, e.g., a leukocyte, lymphocyte, T cell, mast cell, macrophage, etc. In another embodiment, the isolated cell is a cancer cell. In another embodiment, the cell is part of an isolated tissue or a tissue culture. In a further embodiment, the cell can be present in an animal, e.g., an animal that is a disease model or a subject in need of treatment.

In one embodiment, the step of contacting (e.g., binding) the calcium channel with a polypeptide comprises delivering the polypeptide or a functional fragment or homolog thereof to a cell comprising the calcium channel.

In one embodiment, the polypeptides or fragments or homologs thereof of the invention are administered directly to a subject. Generally, the compounds of the invention will be suspended in a pharmaceutically-acceptable carrier (e.g., physiological saline) and administered orally or by intravenous infusion, or administered subcutaneously, intramuscularly, intrathecally, intraperitoneally, intrarectally, intravaginally, intranasally, intragastrically, intratracheally, or intrapulmonarily. In another embodiment, the intratracheal or intrapulmonary delivery can be accomplished using a standard nebulizer, jet nebulizer, wire mesh nebulizer, dry powder inhaler, or metered dose inhaler. They can be delivered directly to the site of the disease or disorder, such as lungs, kidney, or intestines. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 µg/kg. Wide variations in the needed dosage are to be expected in view of the variety of polypeptides, fragments, and homologs available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150-, or more fold). Encapsulation of the polypeptides, fragments, and homologs in a suitable delivery vehicle (e.g., polymeric microparticles or implantable devices) may increase the efficiency of delivery, particularly for oral delivery.

According to certain embodiments, the polypeptide or a functional fragment or homolog thereof can be targeted to specific cells or tissues in vivo. Targeting delivery vehicles, including liposomes and targeted systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry* 25:5500 (1986); Ho et al., *J. Biol. Chem.* 262:13979 (1987); Ho et al., *J. Biol. Chem.* 262:13973 (1987); and U.S. Pat. No. 4,957, 735 to Huang et al., each of which is incorporated herein by reference in its entirety).

Another aspect of the invention relates to a method of inhibiting airway smooth muscle contraction, comprising contacting the airway with the polypeptide or a functional fragment or homolog of the invention, thereby inhibiting airway smooth muscle contraction Inhibition of smooth muscle contraction can be measured by any technique known in the art or disclosed herein. Inhibition of contraction is measured relative to the level of contraction in the absence of contact with the polypeptide or a functional fragment or homolog of the invention. In some embodiments, contraction is inhibited by at least about 10%, e.g., at least about 10%, 20%, 30%, 40%, 50%, 60%, 70%, 80%, 90%, or more.

Another aspect of the invention relates to a method of inhibiting airway hyperreactivity, comprising contacting the airway with the polypeptide or a functional fragment or homolog of the invention, thereby inhibiting airway hyperreactivity. Airway reactivity can be measured by any technique known in the art or disclosed herein. Inhibition of hyperreactivity is measured relative to the level of reactivity in the absence of contact with the polypeptide or a functional fragment or homolog of the invention. "Hyperreactivity," as used herein, refers to increased reactivity of the airway to calcium relative to the level of reactivity of normal airway. In some embodiments, hyperreactivity is inhibited by at least about 10%, e.g., at least about 10%, 20%, 30%, 40%, 50%, 60%, 70%, 80%, 90%, or more.

Another aspect of the invention relates to a method of inhibiting an immune response in a subject, comprising delivering to the subject the polypeptide or a functional fragment or homolog thereof of the invention, thereby inhibiting the immune response. In some embodiments, the immune response is inhibited by at least about 10%, e.g., at least about 10%, 25%, 50%, 75%, or more. Inhibition of the immune response can be quantitated by methods known in the art, e.g., by measurement of the level of immune system cells and/or antibodies in the blood or in the tissue of a subject.

An additional aspect of the invention relates to a method of inhibiting inflammation in a subject, comprising delivering to the subject the polypeptide or a functional fragment or homolog thereof of the invention, thereby inhibiting the inflammation. In some embodiments, the inflammation is inhibited by at least about 10%, e.g., at least about 10%, 25%, 50%, 75%, or more. Inhibition of inflammation can be quantitated by methods known in the art, e.g., by measurement of the level of immune system cells, interleukins, chemokines, or other biological effector molecules in the blood or in the tissue of a subject. Inflammatory disorders that may be treated by methods of the invention include, without limitation, lung disorders such as asthma, chronic obstructive pulmonary disease, idiopathic pulmonary fibrosis, cystic fibrosis, non-cystic fibrosis bronchiectasis, and acute or chronic bronchitis.

A further aspect of the invention relates to a method of treating or preventing an autoimmune disease associated with a calcium channel (e.g., Orai1, Orai3) in a subject in need thereof, comprising contacting the subject with a therapeutically effective amount of the polypeptide or a functional fragment or homolog thereof of the invention, thereby treating or preventing the autoimmune disease. As used herein, an "autoimmune disease associated with a calcium channel" refers to autoimmune diseases or symptoms thereof that are caused by aberrant expression or mutation of a calcium channel or of other factors that activate or inhibit a calcium channel, e.g., STIM1, STIM2). Examples of autoimmune disease associated with a calcium channel (e.g., Orai1, Orai3) include, without limitation, asthma, Sjörgren's syndrome, rheumatoid arthritis, diabetes, autoimmune central nervous system inflammation, and multiple sclerosis.

Another aspect of the invention relates to a method of treating or preventing a cancer associated with a calcium channel (e.g., Orai1, Orai3) in a subject in need thereof, comprising contacting the subject with a therapeutically effective amount of the polypeptide or a functional fragment or homolog thereof of the invention, thereby treating or preventing the cancer. The method may include preventing or slowing cancer cell division and/or metastasis. As used herein, a "cancer associated with a calcium channel" refers to cancers (e.g., solid tumors or blood cell cancers) or symptoms thereof that are caused by aberrant expression or mutation of a calcium channel or of other factors that activate or inhibit a calcium channel, e.g., STIM1, STIM2). Examples of cancers associated with a calcium channel (e.g., Orai1, Orai3) include, without limitation, breast, prostate, cervical, colorectal, brain, and skin cancers.

An additional aspect of the invention relates to a treating or preventing a disorder responsive to inhibition of calcium influx in an airway in a subject in need thereof, comprising delivering to the subject a therapeutically effective amount of the polypeptide or a functional fragment or homolog thereof or pharmaceutical composition of the invention, thereby treating or preventing the disorder. As used herein, the term "disorder responsive to inhibition of calcium influx in an airway," refers to any disease, disorder, or condition that can be treated and/or prevented by inhibiting calcium influx in an airway. The disorder in the methods of the invention can be, in non-limiting examples, asthma or respiratory allergies. In certain embodiments, the polypeptide is delivered by inhalation, e.g., using an inhaler or nebulizer for delivery by oral and/or nasal inhalation.

The polypeptide or a functional fragment or homolog thereof of the present invention can optionally be delivered in conjunction with other therapeutic agents. The additional therapeutic agents can be delivered concurrently with the polypeptide or a functional fragment or homolog thereof of the invention. As used herein, the word "concurrently" means sufficiently close in time to produce a combined effect (that is, concurrently can be simultaneously, or it can be two or more events occurring within a short time period before or after each other). In one embodiment of the invention, the polypeptide or a functional fragment or homolog thereof is delivered to a patient concurrently with a compound that treats and/or prevents asthma, e.g., a bronchodilator such as a β agonist or a steroid. In other embodiments, the polypeptide or a functional fragment or homolog thereof is delivered to a patient concurrently with a compound that treats and/or prevents allergies, e.g., an antihistamine. In certain embodiments, the polypeptide or a functional fragment or homolog thereof is delivered to a patient concurrently with a compound that treats and/or prevents an autoimmune disease, e.g., an immunosuppressant, In certain embodiments, the polypeptide or a functional fragment or homolog thereof is delivered to a patient concurrently with a compound that treats and/or prevents a cancer, e.g., a chemotherapeutic or immunotherapeutic agent, In some embodiments, the combined activity of the polypeptide or a functional fragment or homolog thereof and the other therapeutic agent is superior to the other therapeutic agent alone.

As a further aspect, the invention provides pharmaceutical formulations and methods of administering the same to achieve any of the therapeutic effects (e.g., modulation of calcium influx) discussed above. The pharmaceutical formulation may comprise any of the reagents discussed above in a pharmaceutically acceptable carrier, e.g., a polypeptide or a functional fragment or homolog thereof.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The peptides of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the polypeptide or a functional fragment or homolog thereof (including the physiologically acceptable salts thereof) is typically admixed with, inter alia, an acceptable carrier. The carrier can be a solid or a liquid, or both, and may be formulated with the polypeptide or a functional fragment or homolog thereof as a unit-dose formulation, for example, a metered dose inhaler, which can contain from 0.01 or 0.5% to 95% or 99% by weight of the polypeptide or a functional fragment or homolog thereof. One or more polypeptide or a functional fragment or homolog thereof can be incorporated in the formulations of the invention, which can be prepared by any of the well-known techniques of pharmacy.

A further aspect of the invention is a method of treating subjects in vivo, comprising administering to a subject a pharmaceutical composition comprising a polypeptide or a functional fragment or homolog thereof of the invention in a pharmaceutically acceptable carrier, wherein the pharmaceutical composition is administered in a therapeutically effective amount. Administration of the polypeptide or a functional fragment or homolog thereof of the present invention to a human subject or an animal in need thereof can be by any means known in the art for administering compounds.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). The most suitable route in any given case will depend on the nature and severity of the condition being treated and on the nature of the particular peptide which is being used.

For injection, the carrier will typically be a liquid, such as sterile pyrogen-free water, sterile normal saline, hypertonic saline, pyrogen-free phosphate-buffered saline solution, bacteriostatic water, or Cremophor EL[R] (BASF, Parsippany, N.J.). For other methods of administration, the carrier can be either solid or liquid.

For oral administration, the polypeptide or a functional fragment or homolog thereof can be administered in solid dosage forms, such as capsules, tablets, and powders, or in liquid dosage forms, such as elixirs, syrups, and suspensions. Polypeptides can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the polypeptide or a functional fragment or homolog thereof, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a polypeptide or a functional fragment or homolog thereof of the invention, in a unit dosage form in a sealed container. The polypeptide or a functional fragment or homolog thereof or salt is provided in the form of a lyophilizate which is capable of being reconstituted with a suitable pharmaceutically acceptable carrier to form a liquid composition suitable for injection thereof into a subject. The unit dosage form typically comprises from about 1 mg to about 10 grams of the polypeptide or a functional fragment or homolog thereof or salt. When the polypeptide or a functional fragment or homolog thereof or salt is substantially water-insoluble, a sufficient amount of emulsifying agent which is pharmaceutically acceptable can be employed in sufficient quantity to emulsify the peptide or salt in an aqueous carrier. One such useful emulsifying agent is phosphatidyl choline.

Formulations suitable for rectal administration are preferably presented as unit dose suppositories. These can be prepared by admixing the polypeptide or a functional fragment or homolog thereof with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the polypeptide or a functional fragment or homolog thereof. Suitable formulations comprise citrate or bis/tris buffer (pH 6) or ethanol/water and contain from 0.1 to 0.2M of the compound.

The polypeptide or a functional fragment or homolog thereof can alternatively be formulated for nasal administration or otherwise administered to the lungs of a subject by any suitable means, e.g., administered by an aerosol suspension of respirable particles comprising the polypeptide or a functional fragment or homolog thereof, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the polypeptide or a functional fragment or homolog thereof can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the polypeptide or a functional fragment or homolog thereof can likewise be produced with any solid particulate medicament aerosol generator, by techniques known in the pharmaceutical art.

Alternatively, one can administer the polypeptide or a functional fragment or homolog thereof in a local rather than systemic manner, for example, in a depot or sustained-release formulation.

Further, the present invention provides liposomal formulations of the polypeptide or a functional fragment or homolog thereof disclosed herein and salts thereof. The technology for forming liposomal suspensions is well known in the art. When the polypeptide or a functional fragment or homolog thereof or salt thereof is an aqueous-soluble salt, using conventional liposome technology, the same can be incorporated into lipid vesicles. In such an instance, due to the water solubility of the polypeptide or a functional fragment or homolog thereof or salt, the polypeptide or a functional fragment or homolog thereof or salt will be substantially entrained within the hydrophilic center or core of the liposomes. The lipid layer employed can be of any conventional composition and can either contain cholesterol or can be cholesterol-free. When the polypeptide or a functional fragment or homolog thereof or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the polypeptide or a functional fragment or homolog thereof disclosed herein or salts thereof, can be lyophilized to produce a lyophilizate which can be reconstituted with a pharmaceutically acceptable carrier, such as water, to regenerate a liposomal suspension.

In the case of a water-insoluble polypeptide or a functional fragment or homolog thereof, a pharmaceutical composition can be prepared containing the water-insoluble polypeptide or a functional fragment or homolog thereof, such as for example, in an aqueous base emulsion. In such an instance, the composition will contain a sufficient amount of pharmaceutically acceptable emulsifying agent to emulsify the desired amount of the polypeptide or a functional fragment or homolog thereof. Particularly useful emulsifying agents include phosphatidyl cholines and lecithin.

In particular embodiments, the polypeptide or a functional fragment or homolog thereof is administered to the subject in a therapeutically effective amount, as that term is defined above. Dosages of pharmaceutically active polypeptides can be determined by methods known in the art, see, e.g., *Remington's Pharmaceutical Sciences* (Mack Publishing Co., Easton, Pa.). The therapeutically effective dosage of any specific polypeptide or a functional fragment or homolog thereof will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the polypeptide or a functional fragment or homolog thereof, including the cases where a salt is employed. Toxicity concerns at the higher level can restrict intravenous dosages to a lower level such as up to about 10 mg/kg, with all weights being calculated based upon the weight of the polypeptide or a functional fragment or homolog thereof, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 μmol/kg to 50 μmol/kg, and more particularly to about 22 μmol/kg and to 33 μmol/kg of the polypeptide or a functional fragment or homolog thereof for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults.

The present invention is more particularly described in the following examples that are intended as illustrative only since numerous modifications and variations therein will be apparent to those skilled in the art.

Example 1

Experimental Methods

Human sputum sample collection: All studies were approved by the UNC Institutional Review Board and informed consent obtained from all subjects. Demographic information is included in Table 2. Sputum induction was performed as previously published (Alexis et al., *Clin. Immunol.* 97:21 (2000); Geiser, et al., *J. Innate Immun.* 5:613 (2013)), either by spontaneous expectoration or via sputum induction for different protocols. Sputum was induced with hypertonic saline for sputum collection. Briefly, subjects successively inhaled increasing concentrations of saline (3, 4, and 5% saline) using a Devilbiss UltraNeb 99 ultrasonic nebulizer (Sunrise Medical) and donated sputum after each inhalation session of 7 min. The three sputum samples were pooled.

Animal and measurement of airway resistance: SPLUNC1$^{(-/-)}$ and SPLUNC1$^{(+/+)}$ littermate control mice on the C57BL/6 background were kind gifts from Dr. Y. Peter Di and Dr. Paul B. McCray Jr at University of Pittsburgh, and were bred and housed in housed in a vivarium at Medicine, University of North Carolina at Chapel Hill. Animals were cared for according to the guidelines, and all procedures were approved by UNC Animal Care and Use Committee.

Airway resistance (RAW) was measured in anesthetized mice as previously described (Li et al., *PloS One* 9:e102356 (2014)). Basal resistance measurements were made every 10 seconds for 1 minute prior to serially challenging mice with aerosolized methacholine (Mch) at the following concentrations: 10 mg/mL, 20 mg/mL, and 40 mg/mL. Mice were administered each concentration of Mch for 20 seconds prior to record the RAW using a Flexivent (SCIREQ) at 10 second intervals for 2 minutes immediately following each challenge period.

DNA constructs: Yellow fluorescent protein (YFP) tagged human Orai1 and Myc tagged TRPC3 were gifts from Dr. Craig Montell (Addgene plasmid #25902) and Dr. Anjana Rao (Addgene plasmid #19756), respectively. HA tagged human Orai1 was a generous gift from Dr. Patrick G Hogan at La Jolla Institute for Allergy & Immunology. pcDNA3.1 (+)-V5-SPLUNC1 was a generous gift from Dr. Colin D Bingle at the University of Sheffield.

Cell culture, transfection, and RNA interference: Human airway smooth muscle cells (hASMCs) were generous gift from Dr. Raymond B. Penn at Thomas Jefferson University. Rat ASMCs were provided by Dr. Mohamed Trebak at Pennsylvania State University. Cells were maintained in Dulbecco's Modified Eagle Medium: Nutrient Mixture F-12 (DMEM/F12) (Life Technologies) supplemented with 10% fatal bovine serum (FBS) (Sigma Aldrich) and 0.1% Penicillin-Streptomycin (Life Technologies). HEK293T cells were purchased from ATCC and maintained in DMEM (Life Technologies) in the presence of 10% FBS and 0.1% Penicillin-Streptomycin. Human bronchial epithelial cultures (HBECs) were obtained from freshly excised bronchial specimens from normal and asthmatic subjects and were harvested by enzymatic digestion as previously described under a protocol approved by the University of North Carolina Institutional Review Board (Fulcher et al., *Meth. Mol. Biol.* 945:109 (2013)). Demographic information for healthy and asthmatic donors is included in Table 3. HBECs were cultured at an air-liquid interface in a modified bronchial epithelial growth medium with 5% $CO_2$ at 37° C. and were used 3-4 weeks after the seeding on 12-mm T-clear inserts (Corning).

Short hairpin RNA (shRNA) plasmid against Orai1 and scrambled control shRNA plasmid were purchased from Sigma Aldrich and published previously (Sheridan et al., *J. Biol. Chem.* 288:33509 (2013)). Transfections of all plasmid DNA and shRNA were performed using Lipofectamine 2000 reagent (Life Technologies) according to the manufacturer's instructions.

Antibodies, immunoprecipitation, and immunoblot analysis: Rabbit anti-Orai1, anti-HA epitope (Santa Cruz), anti-GFP, anti-phospho-myosin light chain, anti-total myosin light chain, anti-GAPDH (glyceraldehyde-3-phosphate dehydrogenase) (Cell Signaling Technology); mouse anti-V5 epitope (Life Technologies), were purchased from commercial sources. To detect protein expression in total cell lysates, cells were lysed in Pierce® IP lysis buffer with 25 mM Tris-HCl pH 7.4, 150 mM NaCl, 1% NP-40, 1 mM EDTA, 5% glycerol, followed by SDS-polyacrylamide electrophoresis and immunoblot.

For immunoprecipitation, cell lysates were collected at 48 h post-transfection in Pierce® IP lysis buffer in the presence of 1× protease inhibitor cocktail (PIC) (Roche). Cell lysates were pre-cleared with protein A/G agarose beads and then incubated with 1 µg of antibodies against HA (BioLegend) or V5 (Invitrogen) with protein A/G agarose beads on a rotator at 4° C. overnight. After three washes with IP lysis buffer, immunoprecipitated complexes were eluted in sample buffer (50 mM Tris-HCl [pH 6.8], 2% sodium dodecyl sulfate (SDS), 10% glycerol, 5% (v/v) β-mercaptoethanol (BME), 0.1% bromophenol blue) by heating the samples at 95° C. for 5 min, electrophoresed through SDS-polyacrylamide gels, and subjected to immunoblot analysis.

Calcium imaging: Calcium imaging using fura-2 was adapted from a previous published protocol with minor modifications (Sheridan et al., *J. Biol. Chem.* 288:33509 (2013)). Briefly, hASMCs were loaded with 2 µM fura-2 AM (Invitrogen) and serosal media from HBEC cultures or recombinant SPLUNC1 at 37° C. for 1 h. Cultures were washed with a standard Ringer's solution (101 mM NaCl, 12 mM $NaHCO_3$, 1.2 mM $MgCl_2$, 1.2 mM $CaCl_2$, 0.2 mM KCl, 24 mM HEPES, 10 mM glucose, pH 7.4) or with $Ca^{2+}$-free Ringer's solution as indicated. Cultures were then placed in the Ringer's solution, and images were collected with a 40×1.4 NA oil objective on a Nikon Ti-S inverted microscope. Fura-2 fluorescence was acquired alternately at 340 and 380 nm (emission >450 nm) using LUDL filter wheels, obtained with an Orca FLASH 4.0 CMOS camera (Hammamatsu), and controlled with HCImageLive software. Cell bodies were identified as individual regions of interest (ROIs). Background subtraction was performed using a region without the cell. Signals were converted to relative changes ($F/F_0$) where $F_0$ was the ratio of the average fluorescent intensity (340/380) of ROIs at 0 time point. A total of 20 cells/coverslip were recorded. $\Delta F/F_0$ represents average peak fluorescent intensity changes of three independent experiments.

Myography of Murine Tracheal Rings: Tracheas were excised from 8-week old SPLUNC1 WT and KO mice. After removing excessive connecting tissue, the trachea was cut into ~4-mm rings, mounted on a DMT 620M myography apparatus and allowed to rest in modified Ringer's solution (119 mM NaCl, 4.7 mM KCl, 1.17 mM $MgSO_4$, 1.18 mM $KH_2PO_4$, 2.5 mM $CaCl_2$, 25 mM $NaHCO_3$, 0.027 mM EDTA, 5.5 mM glucose) with continuous oxygenation (95% $O_2$/5% $CO_2$) at 37° C. for 20 min with no applied tension. Optimal passive tension (1 mN) was then applied to the rings. The baseline force was then recorded after stable tension was achieved. The induced contractile force of each ring was assessed by measuring contraction stimulated by 60 mM KCl or 100 mM Ach (unless indicated otherwise), respectively.

Cell contraction assay: The cell contraction assay was performed using a standard commercially available kit (Cell Biolabs). Human ASMCs were harvested and re-suspended in DMEM, two parts of cells were mixed with eight parts of collagen gel lattice mixture and plated for 1 h at 37° C. After the gel solidified, 1 ml of medium was added and incubated for 48 h. Next the gels were released from the sides of wells, and the images were taken using a ChemiDoc™ MP imager (BioRad) at 0 and 1 h after adding indicated reagents. The changes of collagen gel surface areas were analyzed using ImageJ software and normalized to areas of gels at 0 time point.

Protein expression, purification and fluorescent labeling: cDNA of SPLUNC1 and SPLUNC1 truncations was transformed in BL21-Codon Plus competent cells (Agilent Technologies), and purified as previously described (Garland et al., *Proc. Natl. Acad. Sci. USA* 110:15973 (2013)). S18 peptide was synthesized and purified by the UNC Microprotein Sequencing and Peptide Synthesis Facility, as described previously (Hobbs, et al., *Am. J. Physiol. Lung Cell. Mol. Physiol.* 305:L990 (2013)). Fluorescent labeling was done using DyLight 594 or DyLight 633 NHS ester (Thermo) by following manufacture's instruction.

Fluorescent microscopy: Human ASMs were grown on 25-mm glass coverslips for fluorescent imaging. Cells were transfected with the indicated fluorescent-labeled proteins.

At 24 h post-transfection, cells were incubated with or without SPLUNC1 for 4 h, followed by methanol fixation and DAPI (1 µg/ml) staining for nucleus. For live cell imaging, cells were grown on 35-mm glass-bottom dishes (In Vivo Scientific) and transfected with the YFP-Orai1. At 24 h post-transfection, cells were incubated with SPLUNC1 and images were taken at indicated time point. All images were taken with a Leica TCS SP8 63× oil lens using the Leica Application Suite X software (Leica).

Surface labeling and super resolution microscopy: Human ASMs were grown on 22×22 mm² glass coverslips and transfected with the HA-Orai1. 24 h after transfection, cells were fixed with 4% paraformaldehyde (PFA) in PBS, followed by surface labeling with mouse anti-HA antibody (BioLegend) and Alexa 488 goat anti mouse antibody (Life Technologies) at 4° C. After washing with ice cold PBS for five times, cells were incubated with 5 µM SPLUNC1-DyLight 594 for 1 h at 4° C. prior to imaging.

Prior to mounting, 90 µl of oxygen depleting medium, β-Mercaptoethylamine (MEA) was added to the cavity of depression slides. Coverslips were then mounted on the depression slides and sealed with twinsil (Picodent). Super resolution images were captured with a commercial LEICA GSD super-resolution microscope. Ground state depletion (GSD) was performed using 488 nm and 642 nm m solid-state lasers. Samples were excited using 488 nm and 642 nm lasers and sample acquisition was increased with back-pumping using the 405 nm laser as per the manufacturer's instructions. The microscope was fitted with a 160× oil-immersion objective lens.

Fluorescent SPLUNC1 binding assay: Human ASMCs were transfected with scrambled control shRNA and Orai1 shRNA respectively. 72 h post transfection, cells were treated with or without SPLUNC1-DyLight 633 for 1 h, then washed for 5 times with ice-cold Ringer's solution. ASMC-bounded SPLUNC1-Dylight 633 was detected by fluorescent plate reader (Tecan). Cells were also stained with calcein AM (Life Technologies) as cell number control. Relative fluorescent intensity was calculated by normalizing fluorescent intensity at 658 nm to 526 nm.

Surface biotinylation: hASMCs were treated with or without SPLUNC1 for 4 h. Cells were then washed with prechilled PBS$^{++}$ (phosphate buffered saline supplemented with 1 mM $CaCl_2$ and 1 mM $MgCl_2$), and then labeled with 0.5 mg/ml sulfo-NHS-biotin (Thermo) in borate buffer (85 mM NaCl, 4 mM KCl, 15 mM $Na_2B_4O_7$, pH 9.0) while tumbling gently for 30 min on ice. hASMCs were incubated in PBS$^{++}$ buffer supplemented with 10% FBS for 20 min at 4° C. to quench free biotin. Cells were washed again three times with chilled PBS$^{++}$ and proteins were extracted as previously using lysis buffer (0.4% sodium deoxycholate, 1% NP-40, 50 mM EGTA, 10 mM Tris-Cl, pH 7.4) supplemented with 1×PIC. Total inputs were taken from whole cell samples representing 4% of total protein. Solubilized proteins were incubated with 100 µl of neutravidin beads (Pierce) overnight while rotating at 4° C. Samples were washed three times with lysis buffer. Bead-bound proteins were then eluted and SDS-polyacrylamide gels, and subjected to immunoblot analysis.

Measurement of $Ca^{2+}$ signaling in HEK293T cells: HEK293T cells were cultured in 384-well black plates (Costar) at a density of 15,000 cells/well in 50 µl of media (DMEM supplemented with 10% FBS and pen/strep) and incubated overnight at 37° C./5% $CO_2$. On day 2, they were then loaded with 5 µM Fluo4 for 1 h and the change in fluorescence was obtained using a Tecan Infinite Pro plate reader at 37° C. Cells were excited at 488±5 nm and emission was obtained at 520±10 nm.

Nasal instillation of α6 peptides to mice: SPLUNC1$^{(-/-)}$ mice were exposed to 2 µg house dust mite extract in 40 µl of PBS intranasally on days 0 and day 7. After this time, they were again challenged intranasally with 20 µg HDM in 40 µl of PBS from day 14 to day 16. We Then 320 µM of the short α6 peptide was added intranasally once per day on day 15 and on day 16 and the animals sacrificed on day 17. Bronchoalveolar lavage total and differential cell counts were performed using a Kwik-Diff™ Stain Kit (Thermo Scientific). After sacrificing the animals, blood was obtained by cardiac puncture and plasma was taken by spinning down whole blood. Serum HDM-specific antibody levels were measured using an enzyme-linked immunosorbent assay (ELISA). Briefly, plates were coated overnight with 0.01% HDM in PBS and blocked with 1% BSA in PBS before the addition of serum samples that had been diluted 1:10 in blocking buffer and standards for 1 h. Plates were washed 6× with PBS containing 0.05% Tween-20 before incubation with biotinylated anti-mouse IgE (Pharmingen) at a concentration of 2 µg/ml for 1 h. Plates were washed an additional six times, streptavidin-HRP (R&D Systems) was added for 30 min and the amount of bound HDM-specific antibody was determined using TMB substrate (Thermo Scientific).

Statistical analysis: All data are presented as the mean±SE for n experiments. Differences between means were tested for statistical significance using paired or unpaired t tests or their non-parametric equivalent as appropriate to the experiment. Differences between groups were judged using ANOVA. From such comparisons, differences yielding P≤0.05 were judged to be significant. Data were presented as the mean±SEM from three independent experiments unless otherwise indicated. The Graphpad Prism software was used for statistical analysis.

Example 2

Identification of Ca-Regulating Peptides

Figure 1A:
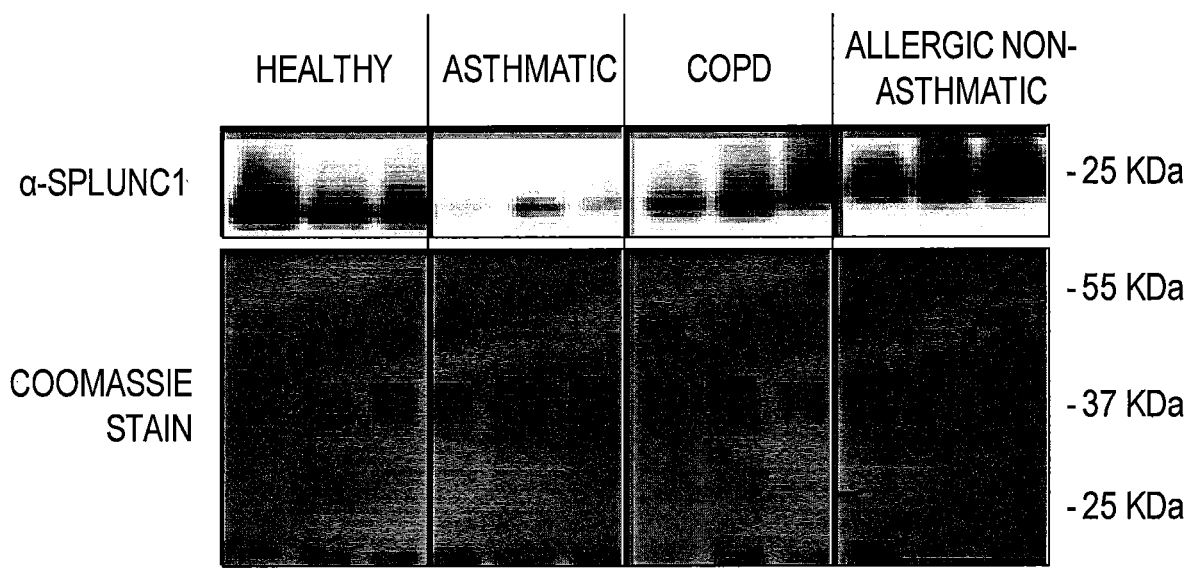
FIGS. 1A-1E show SPLUNC1 is diminished in asthmatic airways and is associated with airway hyperresponsiveness (AHR) in mice. Induced sputum was collected from healthy normal controls, asthmatic and COPD patients, and allergic non-asthmatics. (A) Representative immunoblots of SPLUNC1 (upper) and coomassie loading control (lower). (B) Mean densitometry normalizing intensity of SPLUNC1 to total protein. n=6/group. (C) Evaluation of peripheral airway resistance by Flexivent after methacholine challenge in SPLUNC1$^{(-/-)}$ and SPLUNC1$^{(-/-)}$ litter mate controls. Total airway resistance is expressed in cmH$_2$O.s/ml. * indicates P<0.05 different to control. (D) Tracheal rings (n=6/genotype) were extracted from SPLUNC1$^{(+/+)}$ and SPLUNC1$^{(-/-)}$ mice and mounted onto a wire myograph system. Contraction force was measured under both resting and agonist induced conditions with KCl and Ach. (E) Contractile force was measured pre- and post-SPLUNC1 addition to the bath 1 h prior to agonist addition (all n=6). # and * Indicates P<0.05, ## and ** indicates P<0.01, ### indicates P<0.001.
Figure 1B:
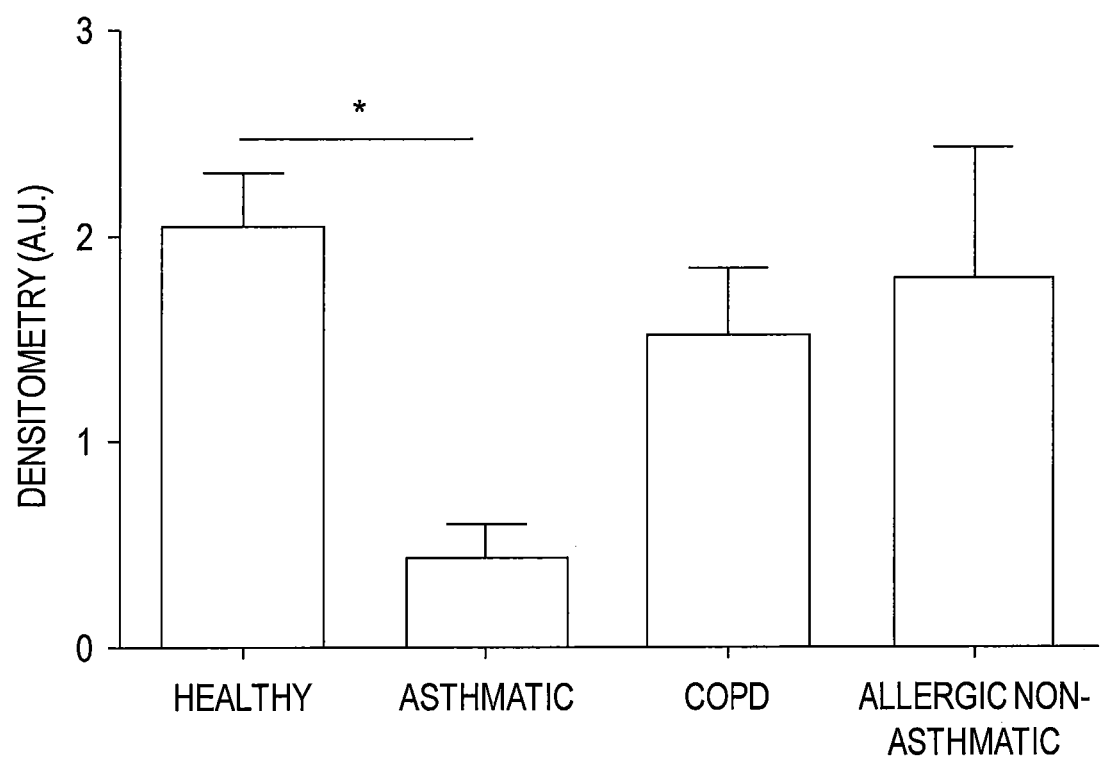
Figure 1C:
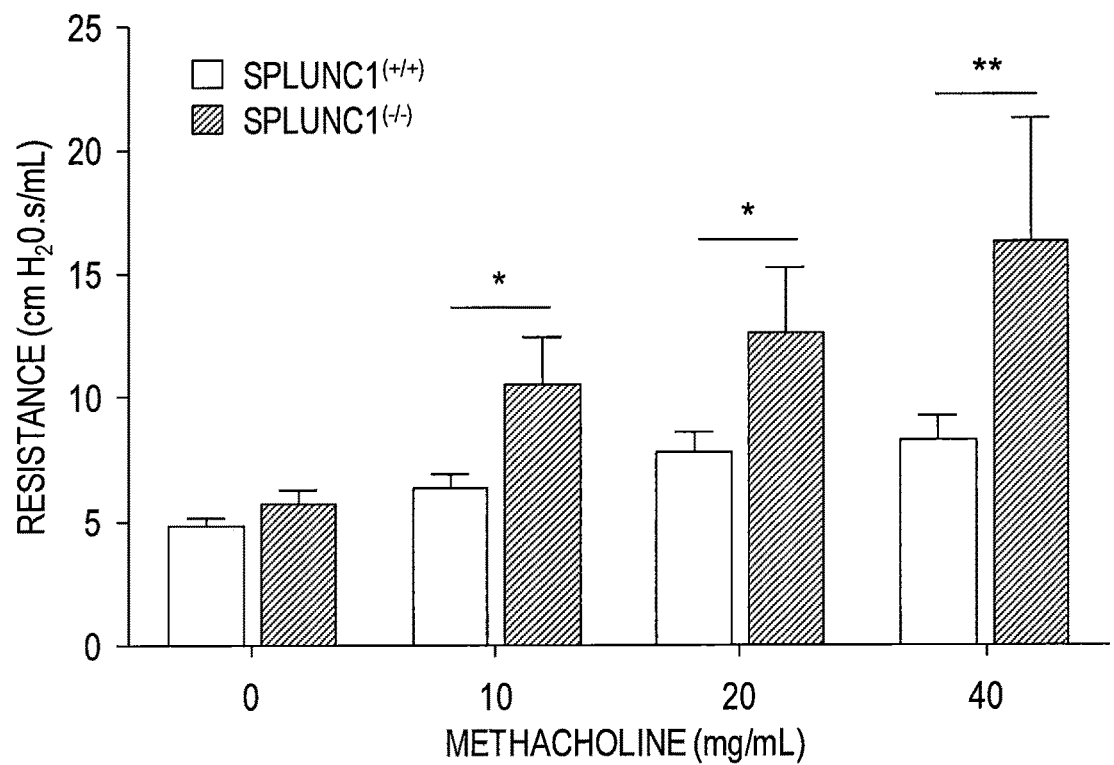
Figure 1D:
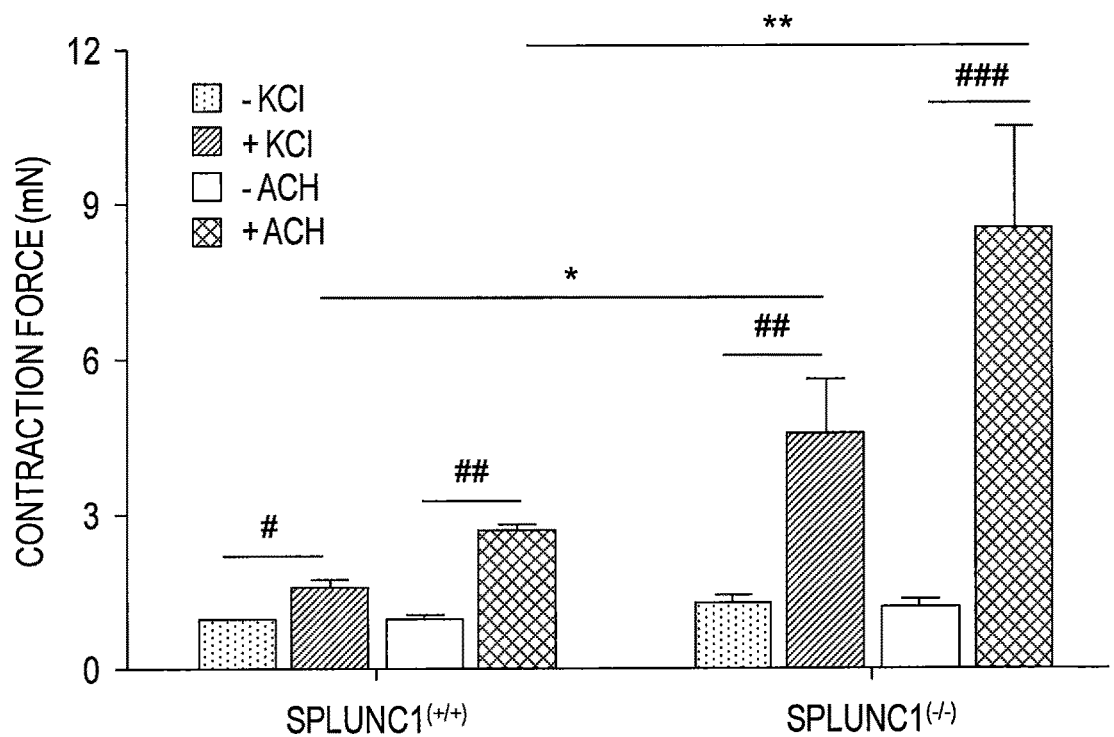
Figure 1E:
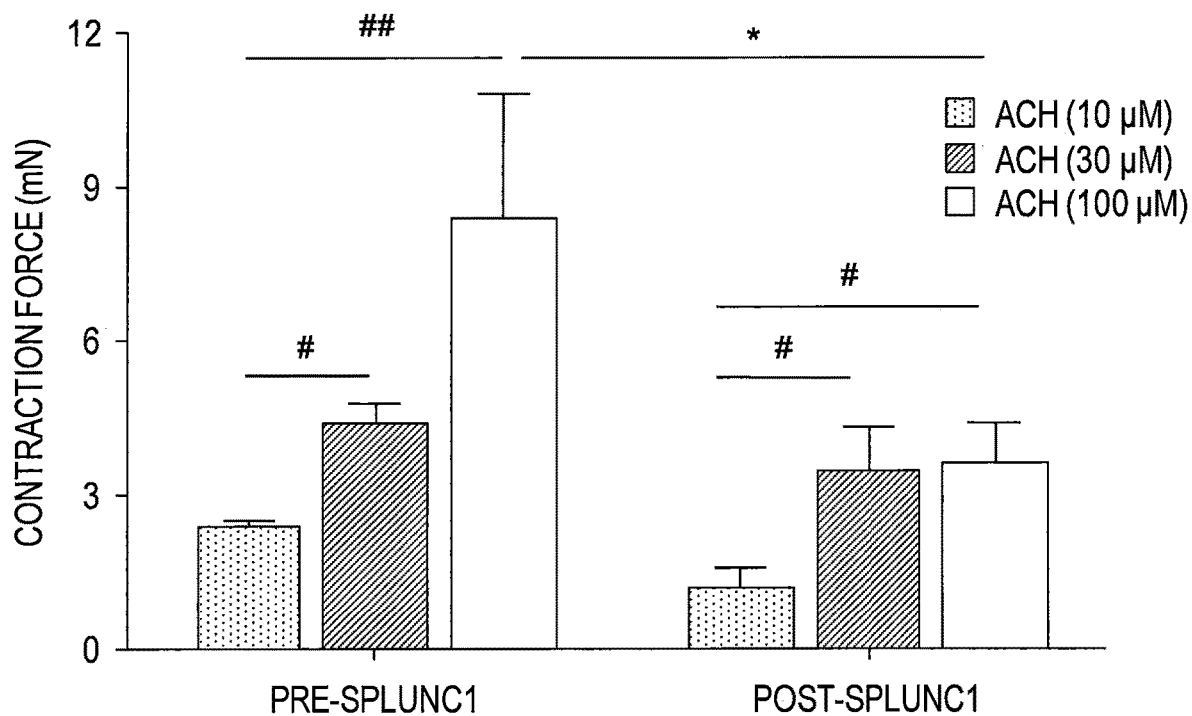
Figure 2A:
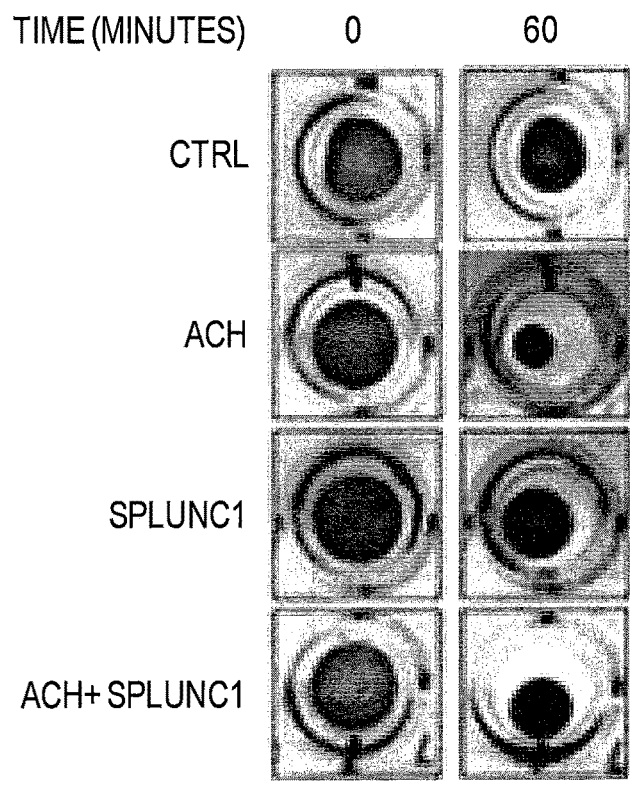
FIGS. 2A-2D show SPLUNC1 decreases airway smooth muscle (ASM) contractility by suppressing myosin light chain (MLC) phosphorylation. Ex vivo tracheal ring contraction was measured by wire-myography. Human ASMCs were grown in a type I collagen matrix in 24 well plates. Contraction of the gel was measured with or without Ach and SPLUNC1. (A) Representative images of gel contraction assay at indicated time points. (B) Summary of contraction data expressed in decrease in gel surface area (%) at 60 min (n=3). (C) Representative immunoblots probed for total and phosphorylated MLC. (D) Mean densitometry taken from (C) (n=3). * Indicates P<0.05, ** indicates P<0.01.
Figure 2B:
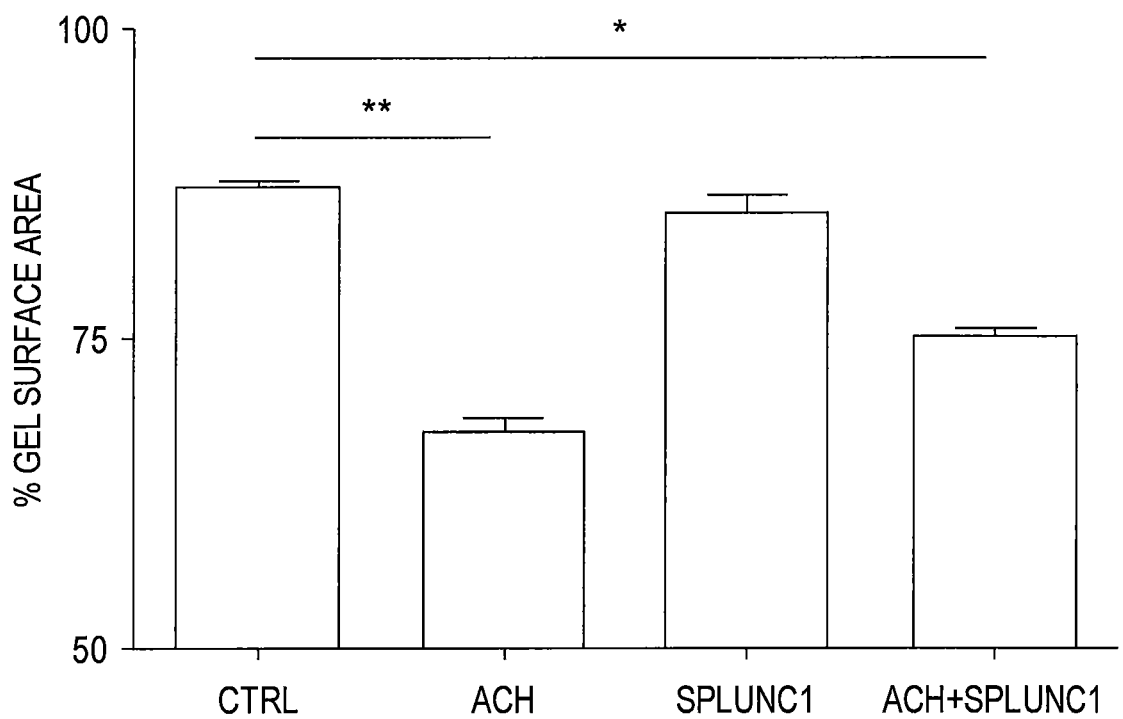
Figure 2C:
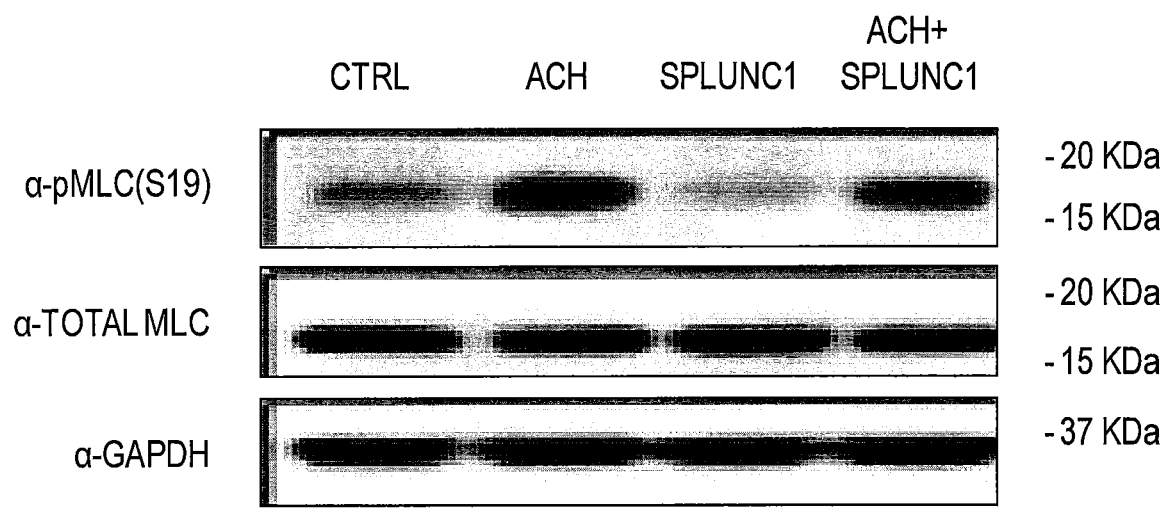
Figure 2D:
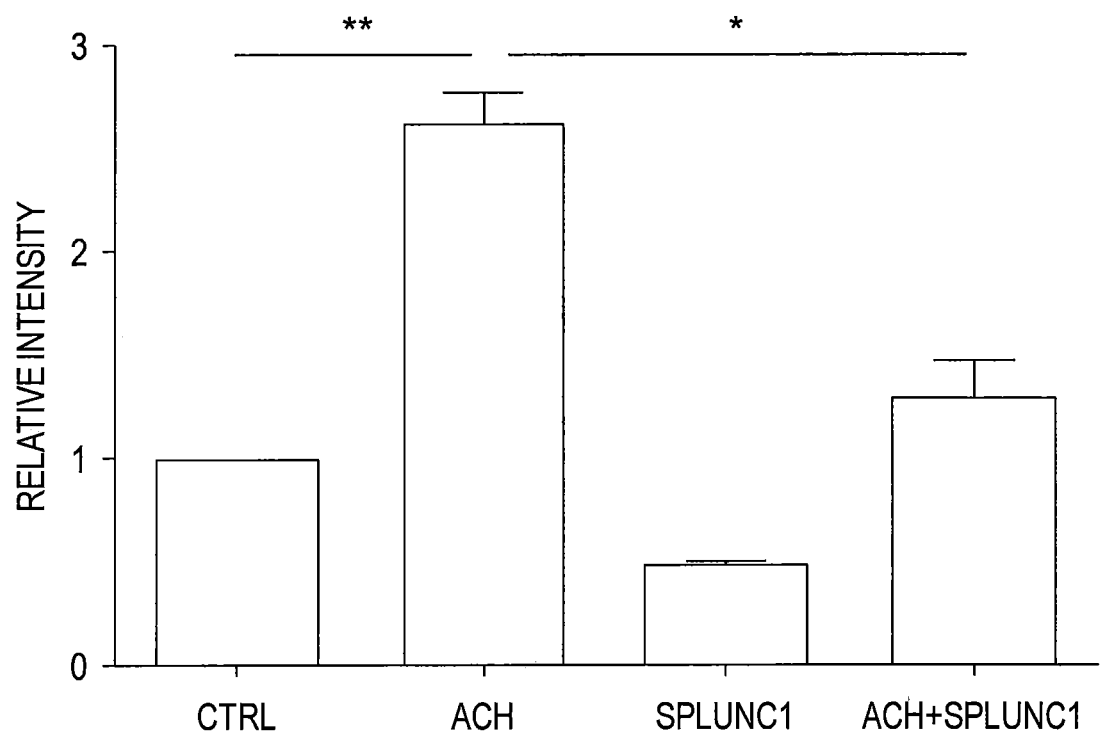
Figure 3A:
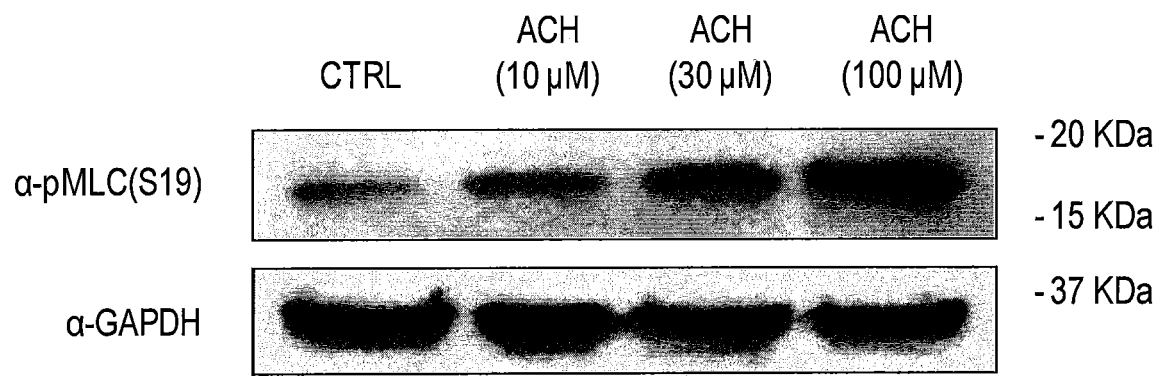
FIGS. 3A-3D show acetylcholine (Ach) increases myosin light chain (MLC) phosphorylation whereas SPLUNC1 decreases MLC phosphorylation in dose dependent-manners. (A) Representative immunoblots showing Ach increases MLC phosphorylation dose-dependently. (B) Intensity of immunoblots from (A) were quantified using Image J, normalized to GAPDH and expressed as relative intensity (n=3). (C) Representative immunoblots probed with phosphorylated MLC antibody. (D) Intensity of immunoblots from (A) were quantified using Image J, normalized to GAPDH and expressed as relative intensity (n=3). * Indicates P<0.05, ** indicates P<0.01.
Figure 3B:
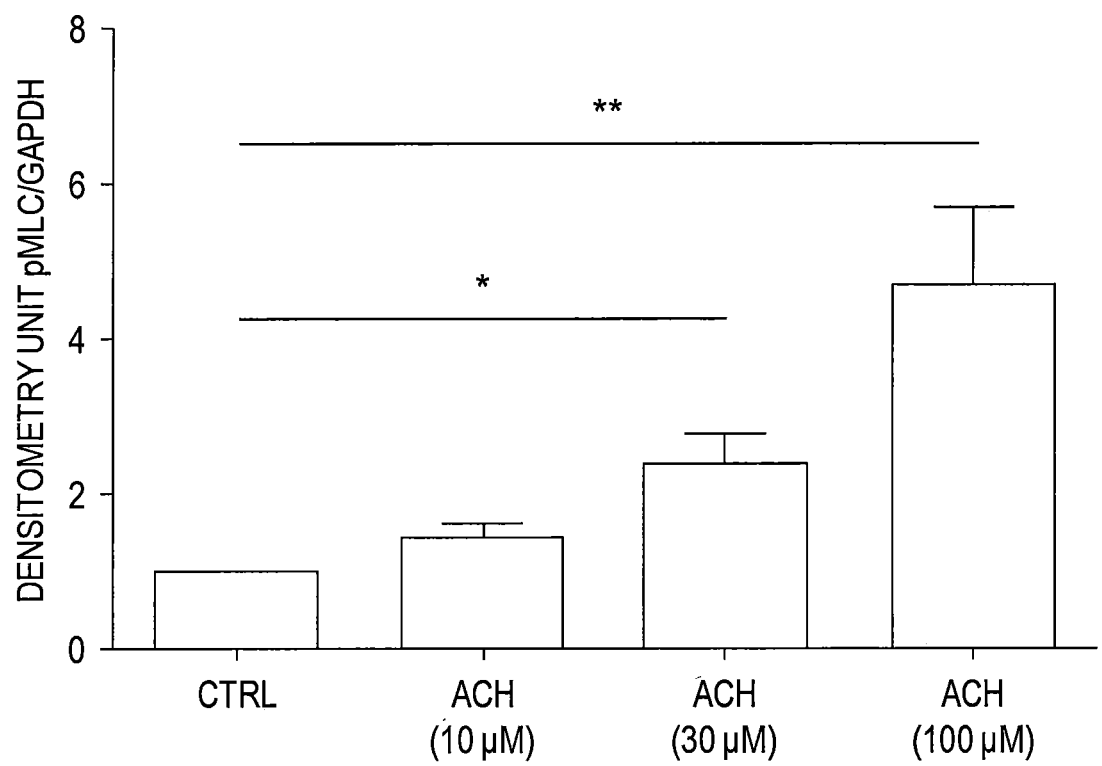
Figure 3C:
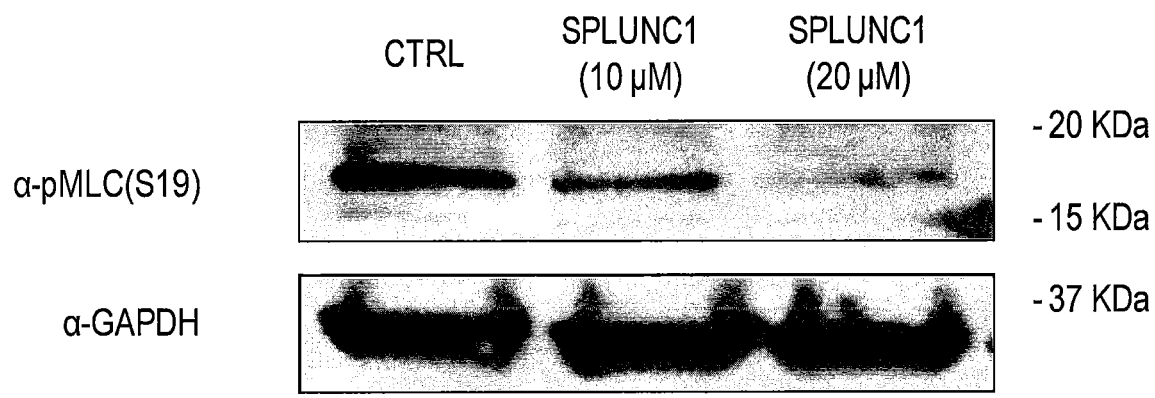
Figure 3D:
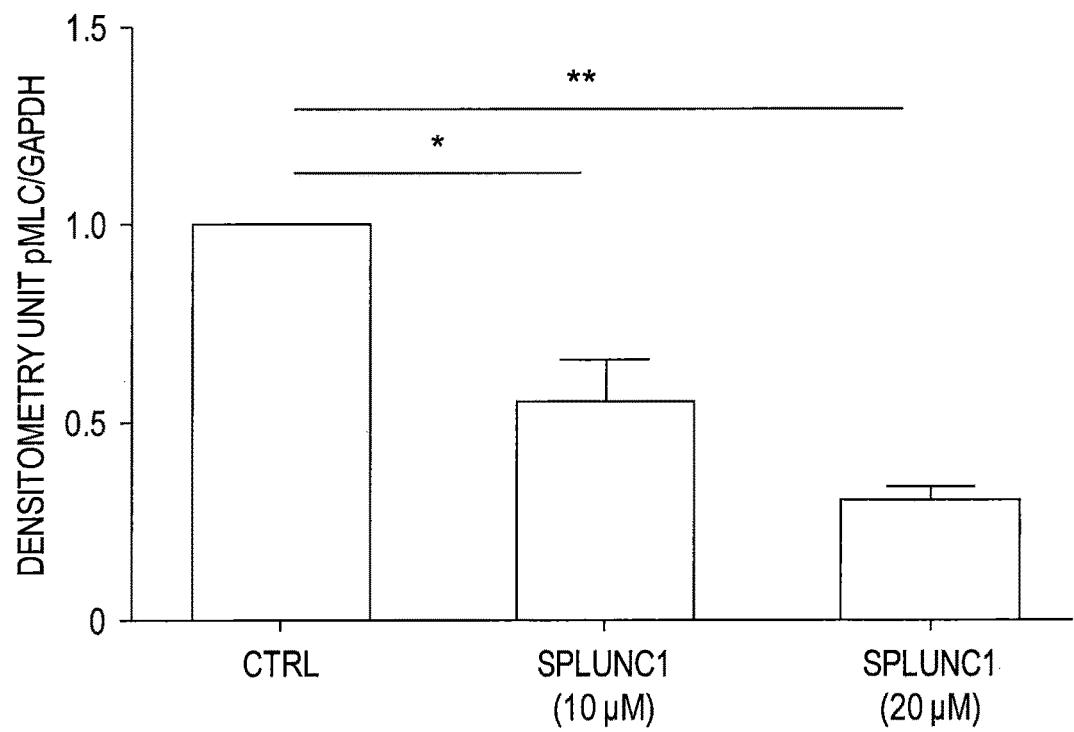

To investigate the role of SPLUNC1 in asthma airway pathogenesis, sputum SPLUNC1 levels were measured in healthy donors, asthmatic patients, chronic obstructive pulmonary disease (COPD) and atopic individuals without asthma, the latter two cohorts serving as disease controls. Demographic information is shown on Table 2. Immunoblot analyses indicated decreased SPLUNC1 protein levels in asthmatic patients' samples compared to the other donors (FIGS. 1A, 1B). To test whether a decrease in SPLUNC1 levels was associated with abnormal ASM activity, it was tested whether SPLUNC1$^{(-/-)}$ mice exhibit AHR. These mice showed a significant increase in airway resistance following methacholine (Mch) challenge compared to their SPLUNC1$^{(+/+)}$ littermate controls (FIG. 1C), indicating an inverse correlation between SPLUNC1 expression and ASM contraction. To further study the effect of SPLUNC1 on ASM, tracheas were excised from these mice and mounted on a wire myograph to measure contractility ex vivo. Tracheal rings from SPLUNC1$^{(-/-)}$ mice showed significant hyper-contractility compared to wildtype controls following exposure to acetylcholine (Ach) or KCl (FIG. 1D). Since this effect was seen with both Ach, which stimulates Nicotinic/Ach receptors, and KCl, which depolarizes the plasma membrane to induce $Ca^{2+}$ influx (Fryer et al., *Am. J. Respiratory Critical Care Med.* 158:S154 (1998); Ratz et al., *Am. J. Physiol. Cell Physiol.* 288:C769 (2005)), it was concluded that this effect was not due to abnormal receptor function. Furthermore, pretreatment with recombinant SPLUNC1 protein for 1 h suppressed contraction (FIG. 1E), suggesting that SPLUNC1 is EDSMRF. Due to the potential importance of this observation, the ASM-SPLUNC1 interaction in ASM cells (ASMC) cultured in a collagen matrix was further investigated. It was observed that ASMC contraction was significantly reduced by pre-incubation with recombinant SPLUNC1 (FIGS. 2A, 2B). In ASMC, contraction is regulated by cross bridge formation between phosphorylated myosin light chain (MLC) and actin. Ach enhances MLC phosphorylation in a $Ca^{2+}$-dependent fashion and therefore enhances contraction. MLC phosphorylation was increased by Ach, whereas pre-treatment with SPLUNC1 decreased both basal and induced MLC phosphorylation (FIGS. 2C, 2D and FIGS. 3A-3D).

TABLE 2

Demographic information of sputum donors in FIG. 1.

| Donor disease status | Age | Gender | FVC | $FEV_1$ | FVC % PRED | $FEV_1$ % PRED |
|---|---|---|---|---|---|---|
| Nonasthmatic/nonallergic/nonsmoker | 21 | M | 6.48 | 5.25 | 117 | 110 |
| Nonasthmatic/nonallergic/nonsmoker | 23 | F | 4.2 | 3.25 | 117 | 105 |
| Nonasthmatic/nonallergic/nonsmoker | 20 | F | 3.64 | 3.08 | 84 | 84 |
| Nonasthmatic/nonallergic/nonsmoker | 23 | M | 6.05 | 4.77 | 106 | 96 |
| Nonasthmatic/nonallergic/nonsmoker | 28 | F | 4.6 | 3.44 | 115 | 102 |
| Nonasthmatic/nonallergic/nonsmoker | 20 | M | 5.15 | 4.1 | 107 | 99 |
| Asthmatic/nonsmoker | 22 | F | 3.76 | 2.93 | 101 | 91 |
| Asthmatic/allergic | 21 | F | 4.27 | 3.26 | 103 | 90 |
| Asthmatic/allergic | 36 | M | 5.85 | 4.66 | 102 | 102 |
| Asthmatic/allergic | 31 | F | 3.52 | 2.8 | 105 | 98 |
| Asthmatic/allergic | 21 | F | 4.84 | 3.65 | 122 | 106 |
| Asthmatic/allergic | 26 | F | 4.74 | 3.32 | 119 | 96 |
| COPD | 62 | F | 2.01 | 1.14 | 74 | 54 |
| COPD | 46 | F | 3.82 | 2.92 | 101 | 96 |
| COPD | 67 | M | 3.92 | 1.82 | 48 | 48 |
| COPD | 70 | F | 2.06 | 1.12 | 72 | 51 |
| COPD | 52 | M | 3.4 | 1.66 | 72 | 45 |
| COPD | 58 | M | 4.21 | 1.2 | 84 | 32 |
| Healthy/allergic | 37 | F | 3.53 | 3.07 | 103 | 108 |
| Healthy/allergic | 25 | F | 4.23 | 3.47 | 115 | 111 |
| Healthy/allergic | 22 | F | 2.89 | 2.59 | 94 | 97 |
| Healthy/allergic | 28 | M | 4.89 | 4.09 | 87 | 87 |
| Healthy/allergic | 27 | M | 4.89 | 3.86 | 98 | 92 |
| Healthy/allergic | 30 | M | 5.02 | 4.18 | 105 | 104 |

Figure 4A:
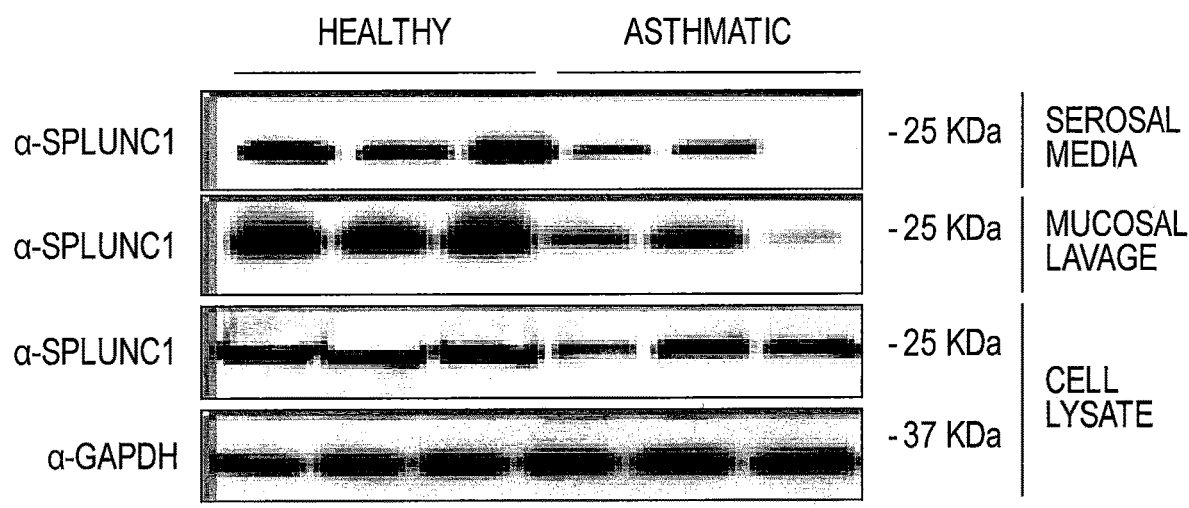
FIGS. 4A-4H shows SPLUNC1 is secreted basolaterally and blocks store operated Ca$^{2+}$ influx in ASMCs. (A) Representative immunoblots showing SPLUNC1 from healthy and asthmatic HBECs. (B) Mean densitometry taken from (A). (C) Representative traces of Ca$^{2+}$ imaging using fura-2. Basolateral media from normal and asthmatic HBECs were co-incubated with human ASMCs for 1 h. (D) Summary of peak fluorescent ratio change in ASMCs incubated with media from healthy and asthmatic HBECs, respectively (n=3/culture). (E) SPLUNC1 inhibits TG induced cytosolic Ca$^{2+}$ increases in a dose-dependent manner. ASMCs were incubated with indicated concentrations of SPLUNC1, and changes in fura-2 emission ratio over time were plotted. Data are expressed in relative changes (F/F$_0$), where F$_0$ was the average fluorescent intensity (340/380) of ROIs at 0 time point. A total of 20 cells/coverslip were recorded. ΔF/F$_0$ represents average peak fluorescent intensity changes of three independent experiments. (F) Representative trace of Ca$^{2+}$ imaging using fura-2. Extracellular Ca$^{2+}$ was chelated using EGTA. Tharpsigargin (TG) was added at the beginning to release Ca$^{2+}$ from the SR. Ca$^{2+}$ was then added back to the buffer at the indicated time point to trigger Ca$^{2+}$ influx. (G) Summary of peak fluorescent ratio change in the presence of TG and extracellular Ca$^{2+}$ (n=3). (H) Summary of peak fluorescent ratio changes when ASMCs were pre-incubated with different truncated SPLUNC1 peptides (n=3/group). * Indicates P<0.05, ** indicates P<0.01.
Figure 4B:
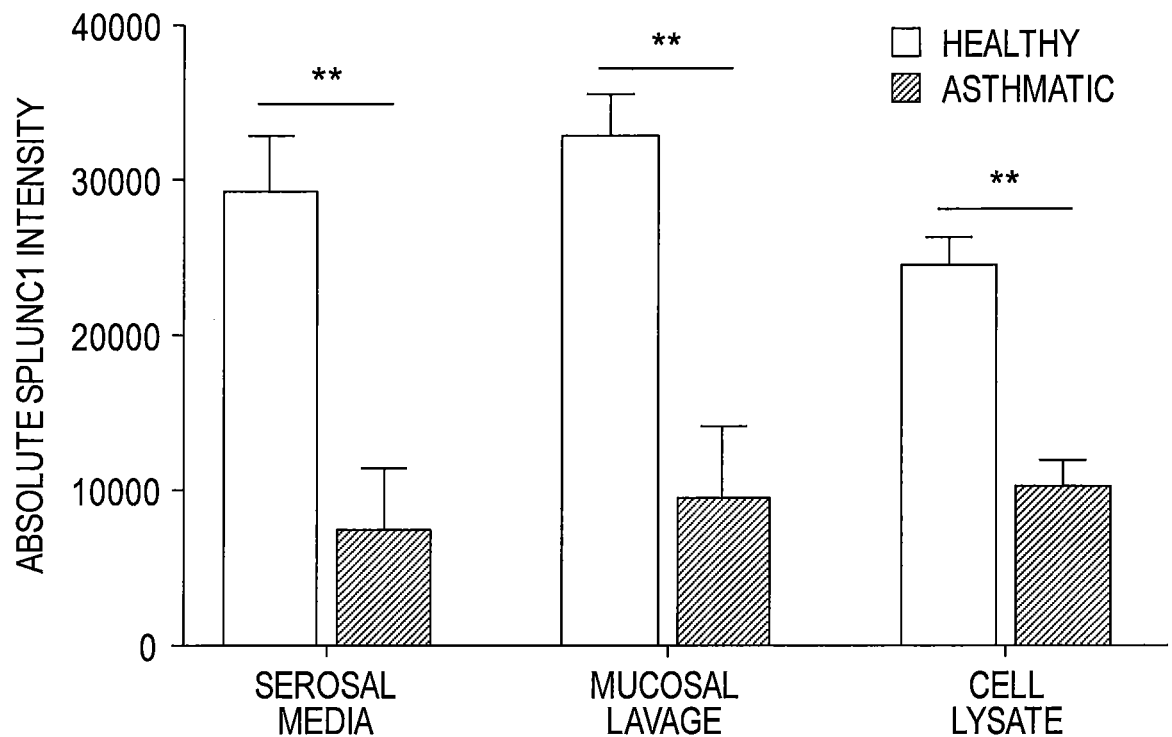
Figure 4C:
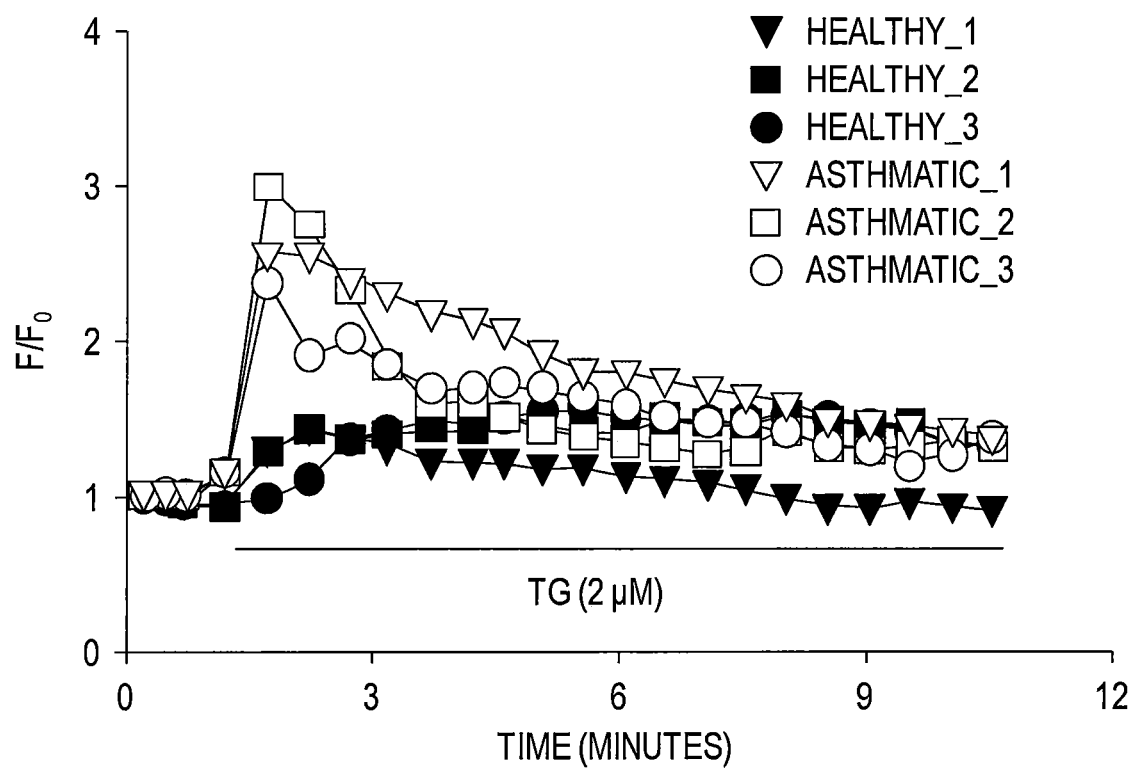
Figure 4D:
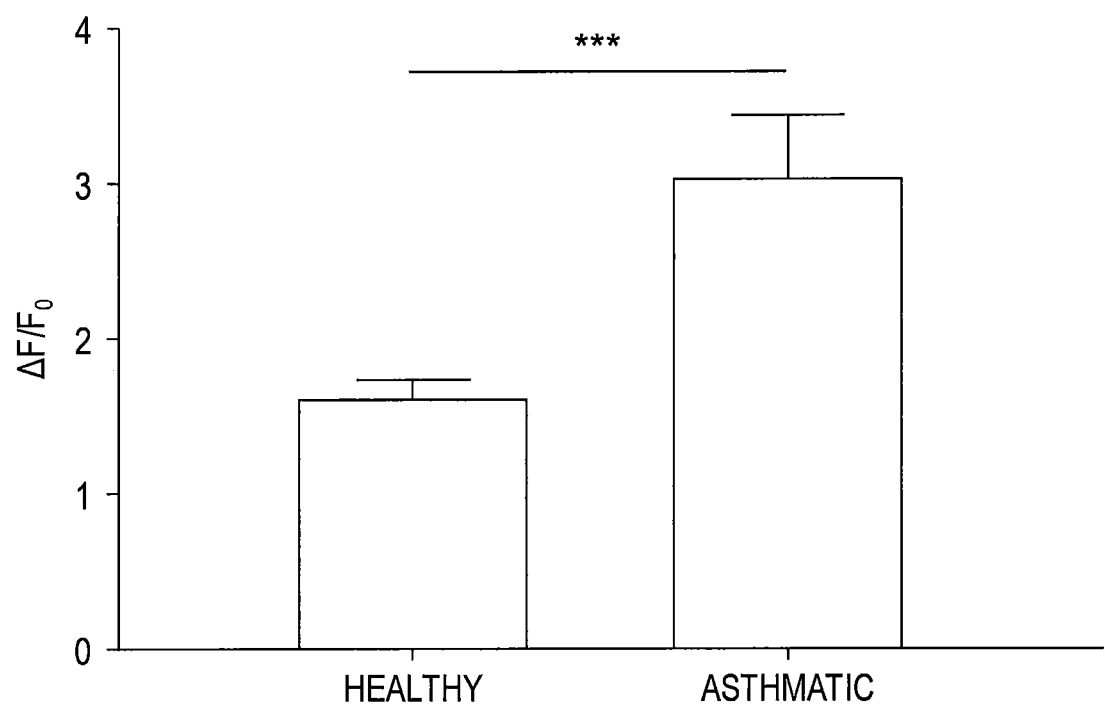
Figure 4E:
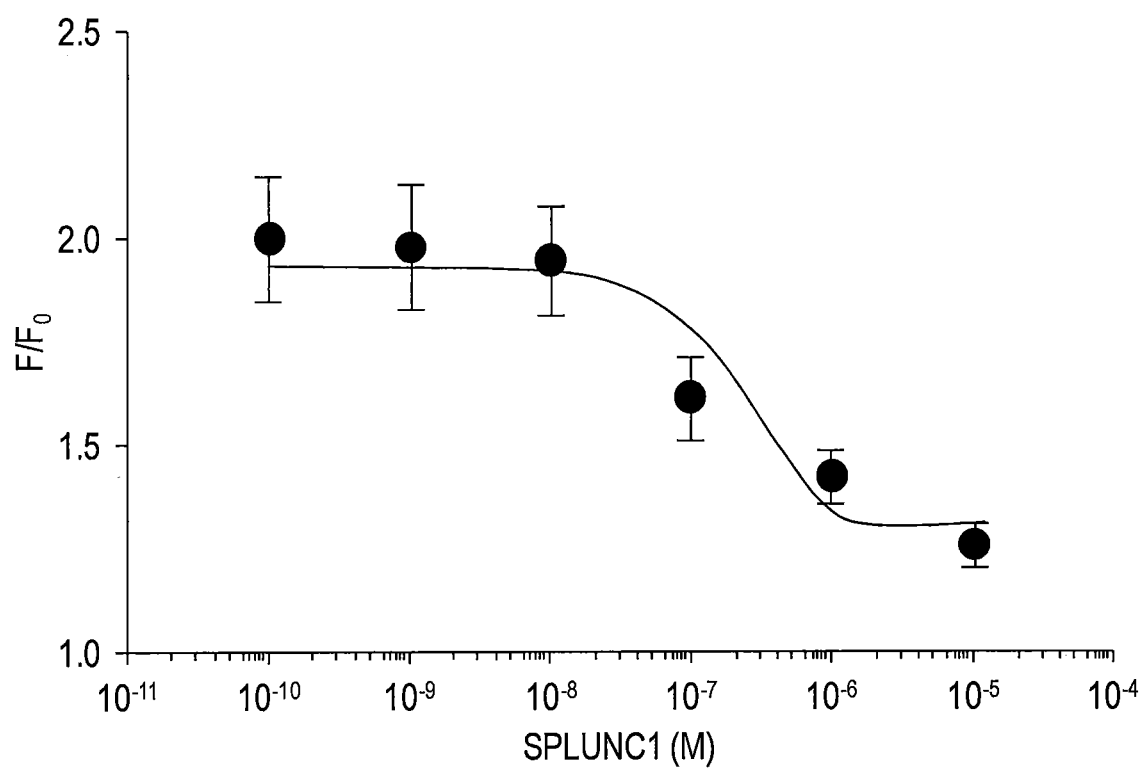
Figure 4F:
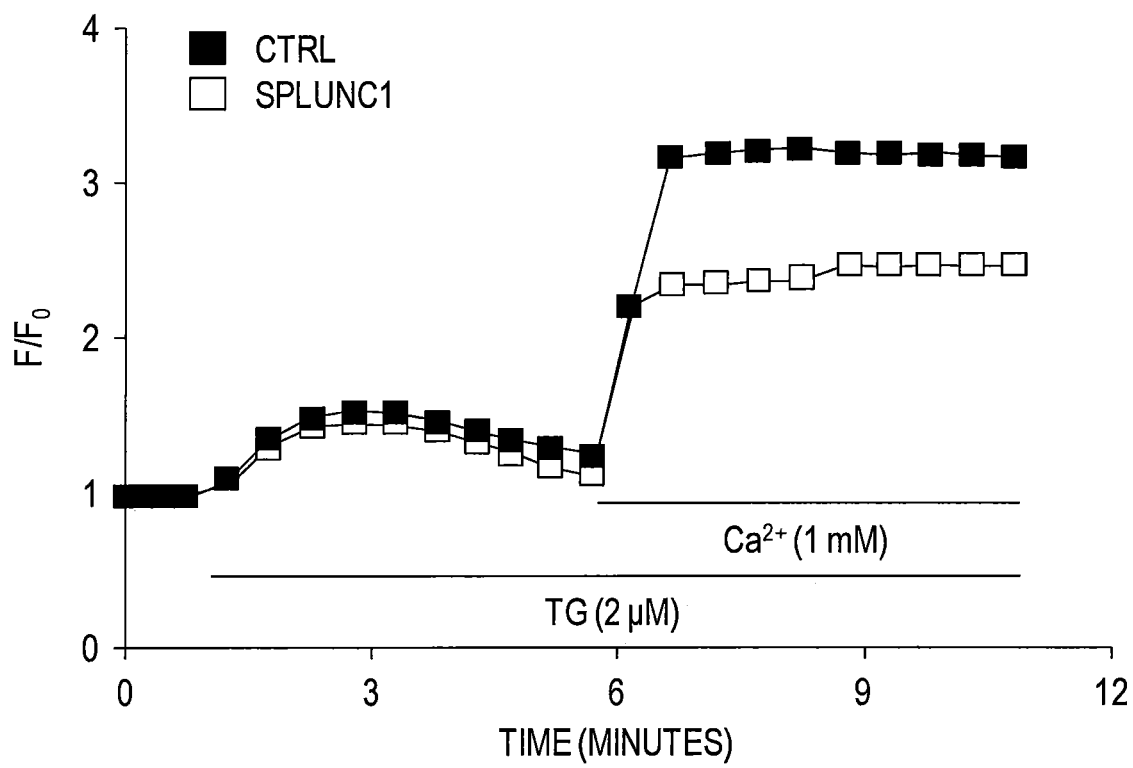
Figure 4G:
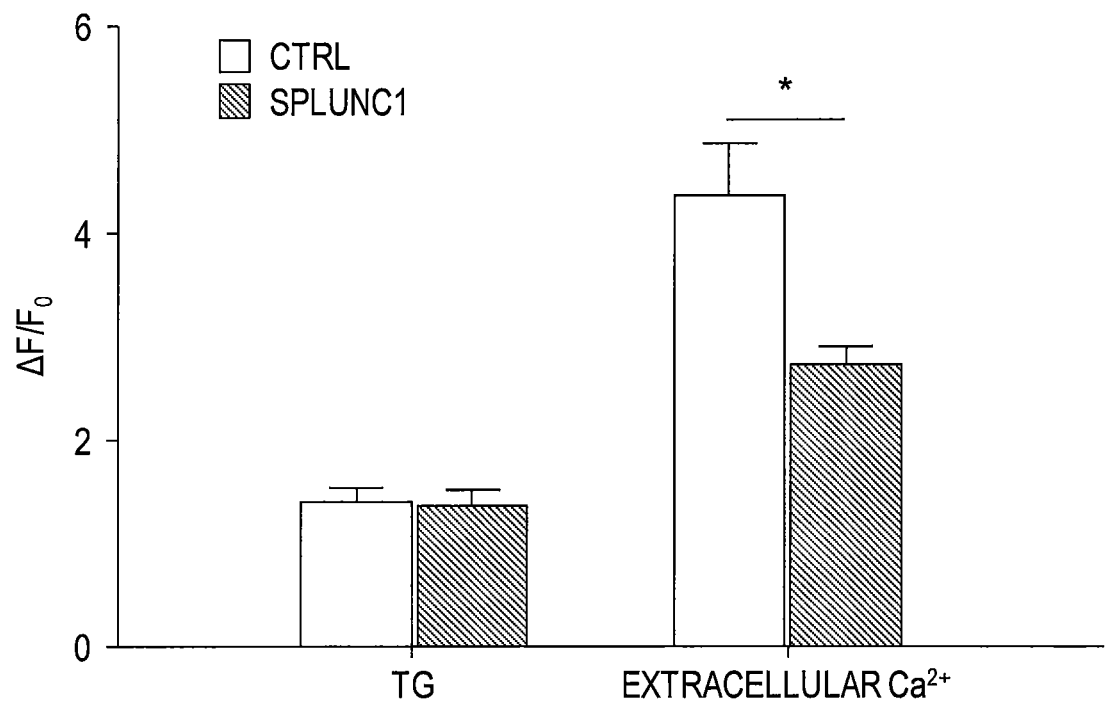
Figure 5:
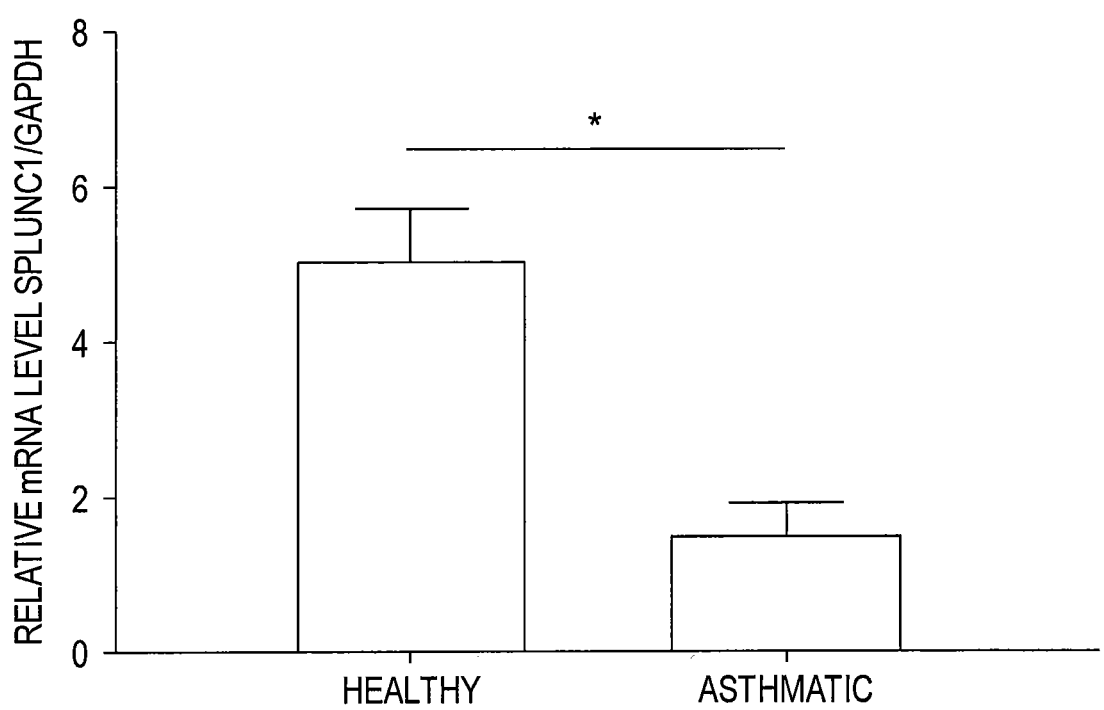
FIG. 5 shows decreased SPLUNC1 mRNA in asthmatic human bronchial epithelial cultures. Total RNA from HBECs was extracted and mRNA levels of SPLUNC1 were measured by qRT-PCR (n=3). * Indicates P<0.05.
Figure 6A:
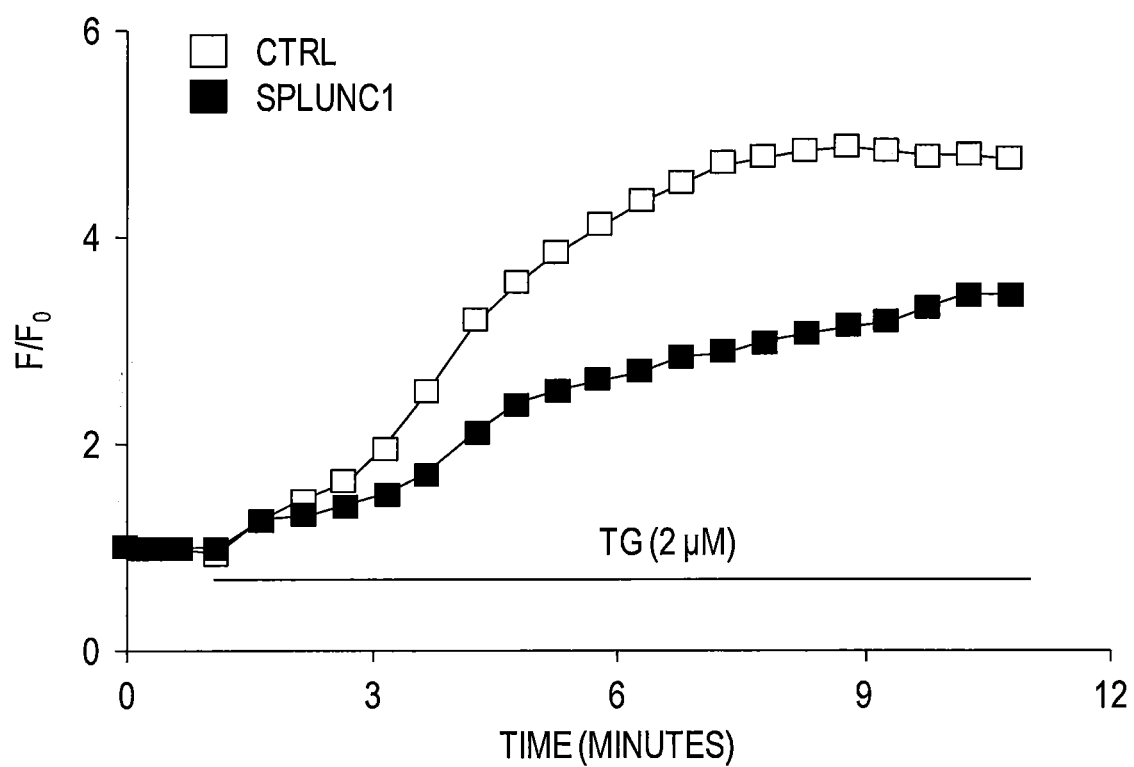
FIGS. 6A-6B show SPLUNC1 suppresses cytosolic Ca$^{2+}$ elevation in the presence of TG. (A) Representative traces of Ca$^{2+}$ imaging. SPLUNC1 was co-incubated with at ASMCs and fura-2 for 1 h. Fura-2 emission ratio was then recorded over time. (B) Summary of peak fluorescent ratio changes of (A) (n=3). * Indicates P<0.05.
Figure 6B:
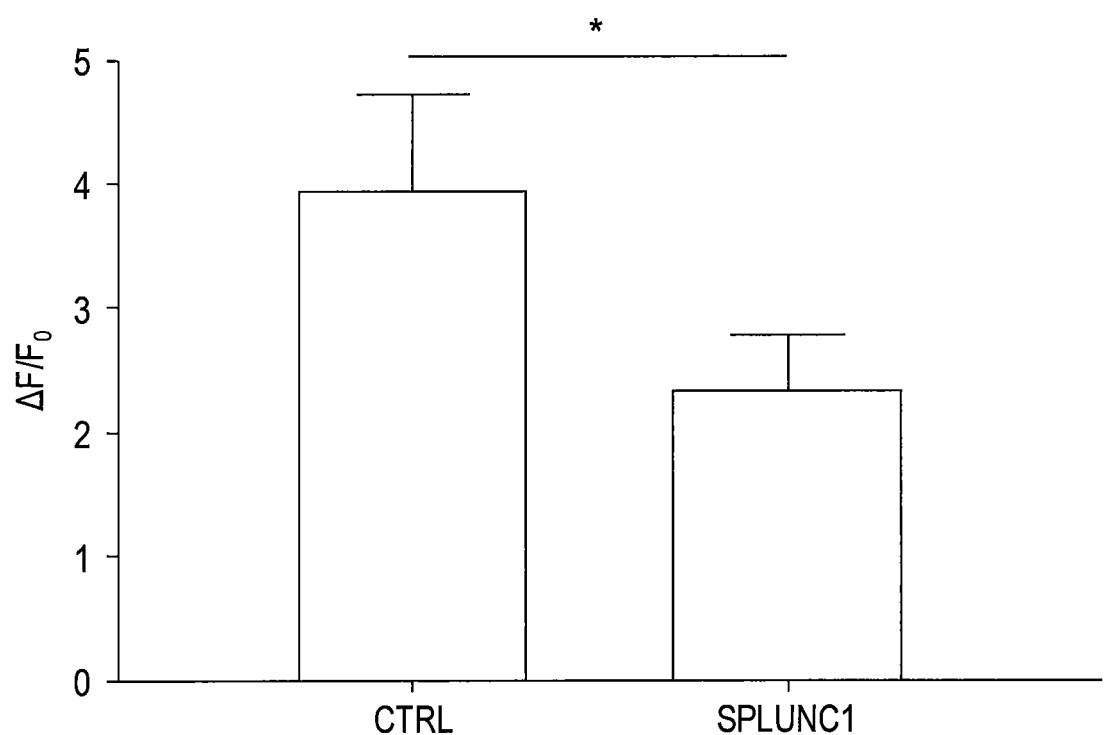

Next, SPLUNC1 protein levels were measured in primary HBECs derived from healthy and asthmatic donors. Demographic information is shown on Table 3. Consistent with the sputum samples data (FIGS. 1A, 1B), immunoblot analyses revealed significantly decreased levels of SPLUNC1 in asthmatic HBEC lysates, serosal media and mucosal lavage (FIGS. 4A, 4B) compared to non-asthmatic donors. A decrease in SPLUNC1 mRNA in asthmatic HBECs was also detected (FIG. 5). Chu et al. previously reported that asthma associated T-helper 2 cell (Th2) cytokines (e.g., IL-13) significantly decreased SPLUNC1 expression in HBECs (Chu et al., *J. Immunol.* 179:3995 (2007)). Based on these data, it is speculated that diminution of SPLUNC1 in asthmatic tissue may be closely associated with the Th-2 response. Since SPLUNC1 downregulated MLC phosphorylation, it was next investigated whether SPLUNC1 regulated ASMC $Ca^{2+}$ signaling. When ASMC were exposed to serosal media from healthy HBECs, or to recombinant SPLUNC1, the tharpsigargin (TG)-induced $Ca^{2+}$ flux was significantly reduced (FIGS. 4C, 4D and FIGS. 6A-6B) in a dose-dependent fashion (FIG. 4E). $Ca^{2+}$ emanates from multiple sources, including the SR and the extracellular milieu (Koopmans et al., *Pulmonary Pharmacol. Ther.* 29:108 (2014)). Without extracellular $Ca^{2+}$, TG only moderately raised cytoplasmic $Ca^{2+}$, whereas reintroduction of $Ca^{2+}$ induced SOCE. Pre-treatment with SPLUNC1 had no effect on SR $Ca^{2+}$ release but significantly suppressed SOCE (FIGS. 4F, 4G).

TABLE 3

Demographic information of sputum donors in FIGS. 4A-4D and 5.

| Donor disease status | Age | Gender |
|---|---|---|
| Healthy/nonasthmatic/non-smoker | 19 | M |
| Healthy/nonasthmatic/non-smoker | 45 | M |
| Healthy/nonasthmatic/non-smoker | 49 | M |
| Asthmatic/smoker | 50 | F |
| Asthmatic/smoker | 25 | M |
| Asthmatic/smoker | 38 | F |

Figure 4H:
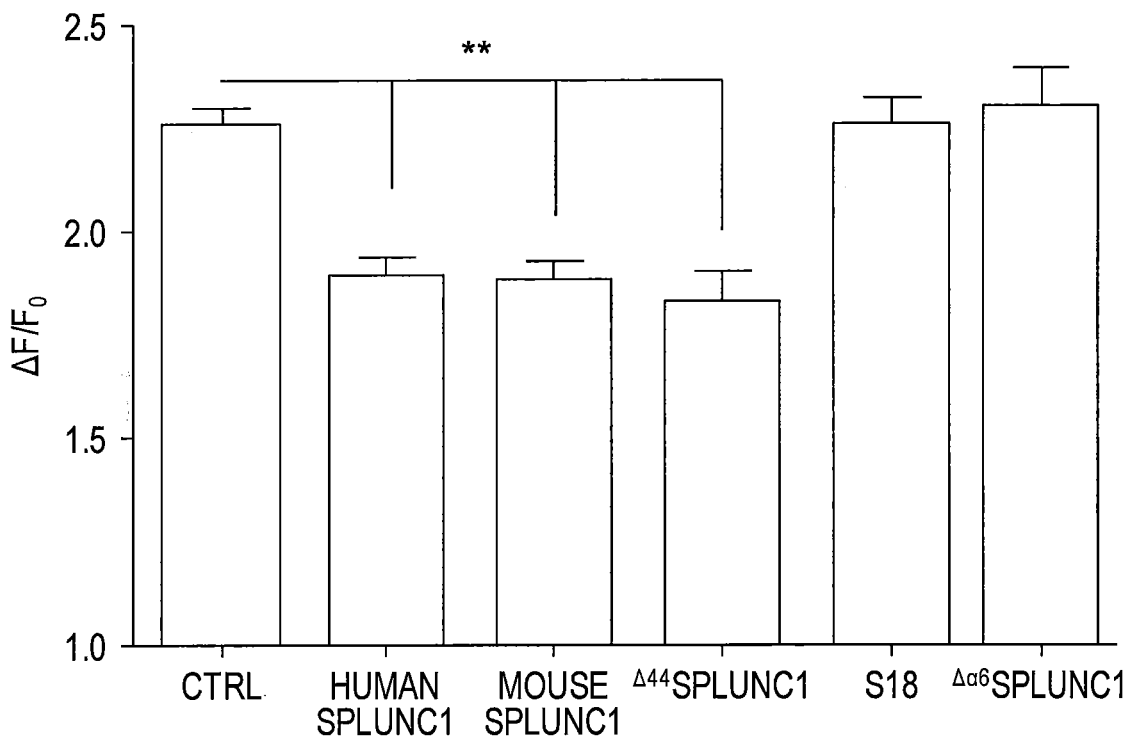

To map out the structural region within SPLUNC1 that was responsible for this effect, a series of SPLUNC1 mutants/peptides was used to test their ability to suppress $Ca^{2+}$ signaling. Inhibition was not different for mouse and human SPLUNC1 (FIG. 4I1). The S18 region of SPLUNC1, which had been previously identified as its ENaC regulatory domain (Hobbs et al., *Am. J. Physiol. Lung Cell. Mol. Physiol.* 305:L990 (2013)), did not inhibit SOCE, suggesting that the action of SPLUNC1 was ENaC independent. Similarly, SPLUNC1 lacking its N-terminal S18 region ($\Delta^{44}$SPLUNC1) still inhibited $Ca^{2+}$ signaling. However, deletion of alpha helix 6 ($\Delta\alpha^6$SPLUNC1) significantly abolished its ability to inhibit $Ca^{2+}$ signaling (FIG. 4H).

Figure 7A:
FIGS. 7A-7H show SPLUNC1 modulates SOCE by interacting with Orai1. (A) and (B) Immunoprecipitation analysis was performed using cell lysates from HEK293T cells cotransfected with V5-SPLUNC1 and HA-Orai1. HA-Orai1 was pulled down by V5-SPLUNC1. V5-SPLUNC1 was pulled down by HA-Orai1 in the HEK293T cell lysate. Data represents three independent immunoprecipitation per condition. (C) Ground state depletion super-resolution images of HA-tagged Orai1 and DyLight 594 labeled SPLUNC1 in ASMCs. Scale bar is 2.5 μm. (E) Human ASMCs were incubated with SPLUNC1, followed by surface biotinylation and immunoblot using indicated antibodies. (F) Mean densitometry of plasma membrane and total Orai1/GAPDH and expressed as relative intensity (n=3). (G) Human ASMCs were transfected with control and Orai1 shRNA respectively. mRNA levels of Orai1 were measured by qRT-PCR. (G) Representative traces of Ca$^{2+}$ imaging using fura-2.
Figure 7A:
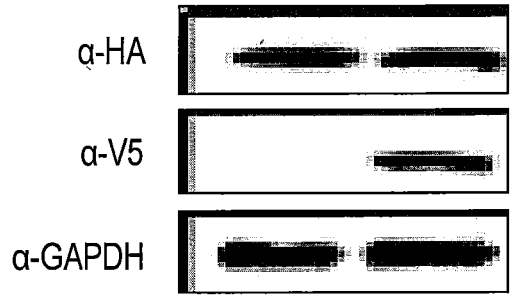
Figure 7B:
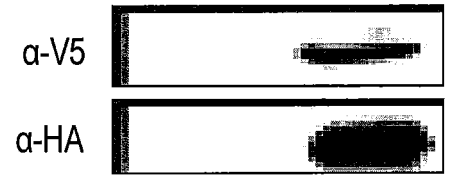
Figure 7B:
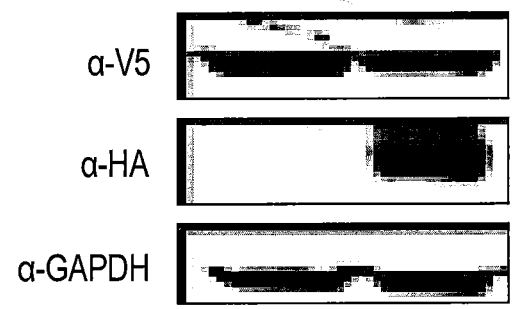
Figure 7C:
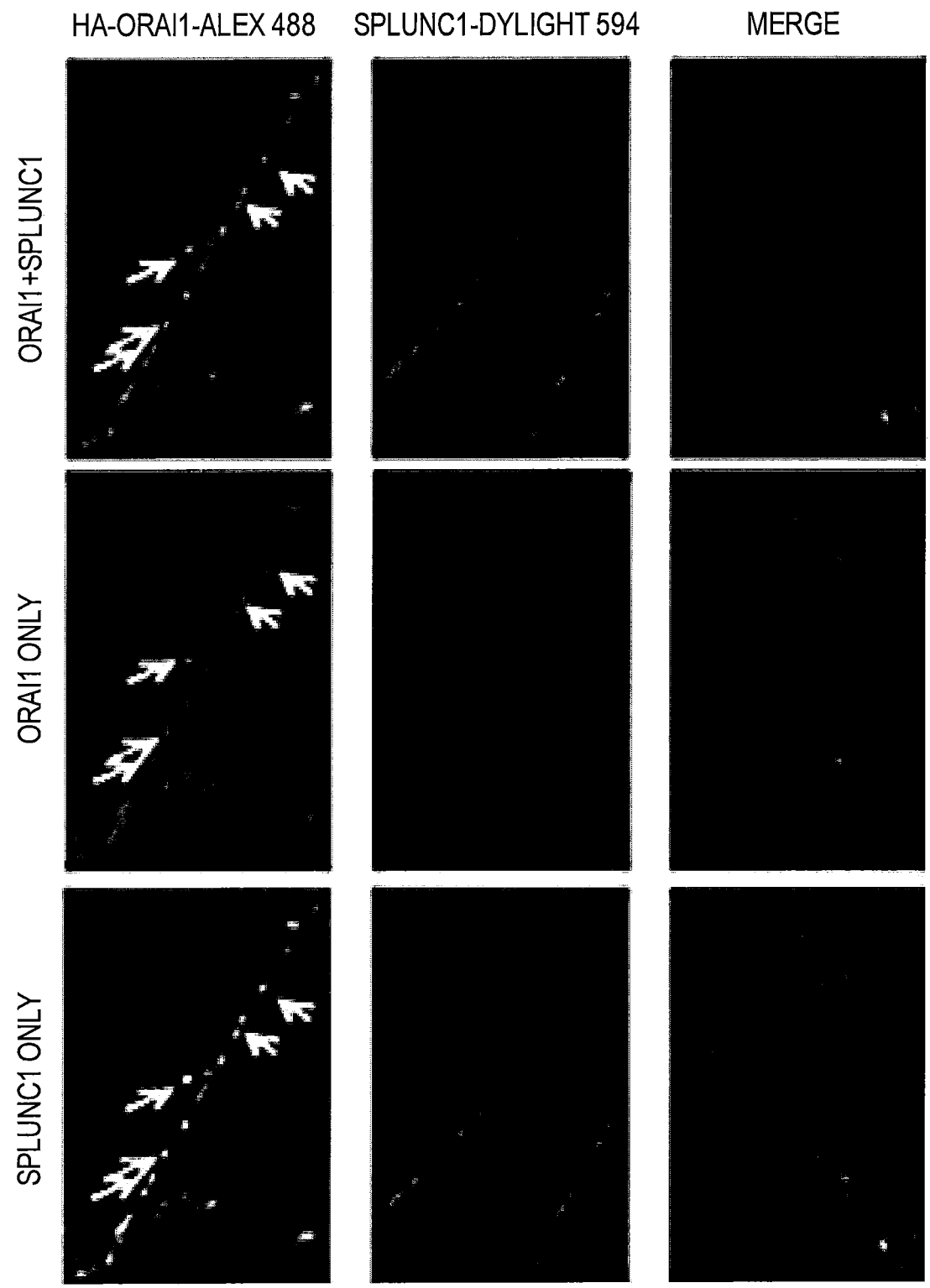
Figure 7D:
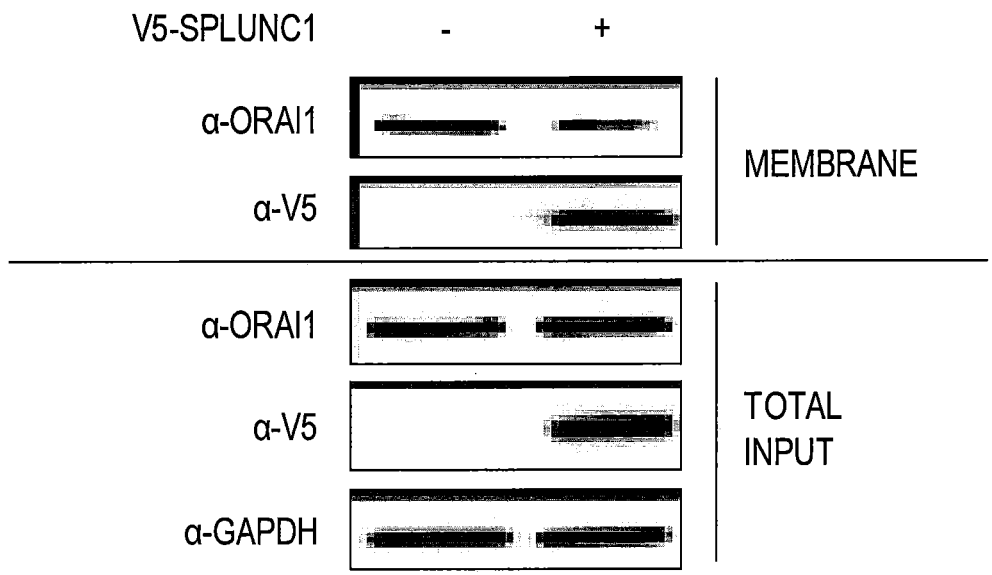
Figure 7E:
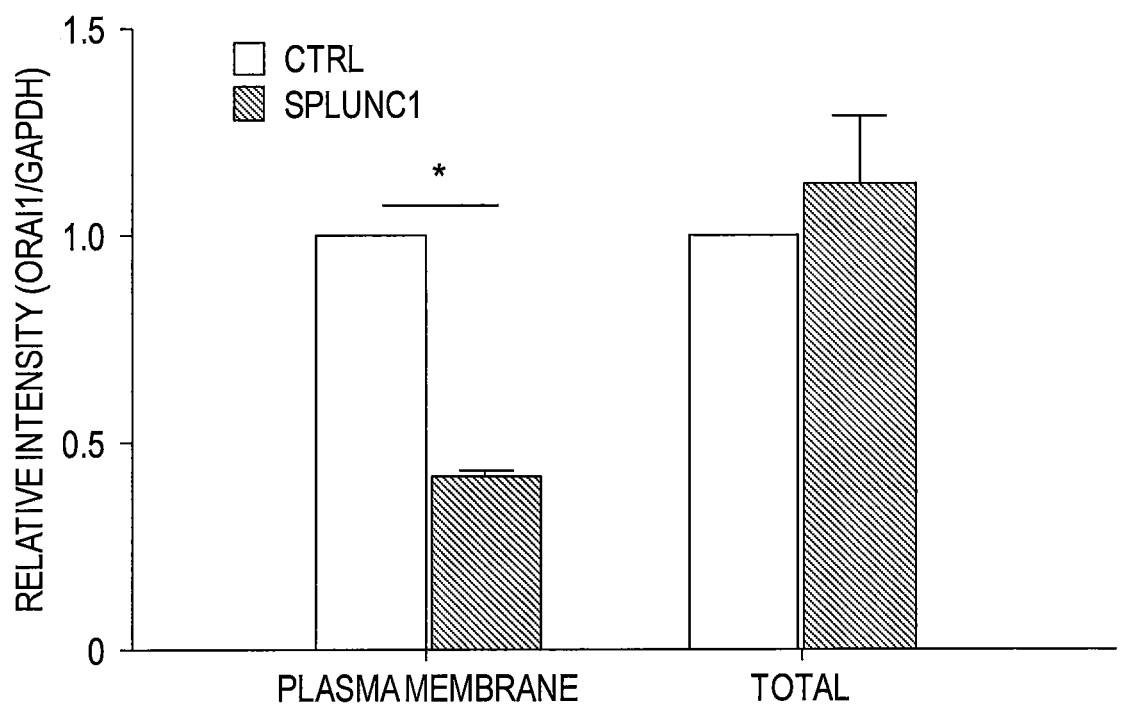
Figure 7F:
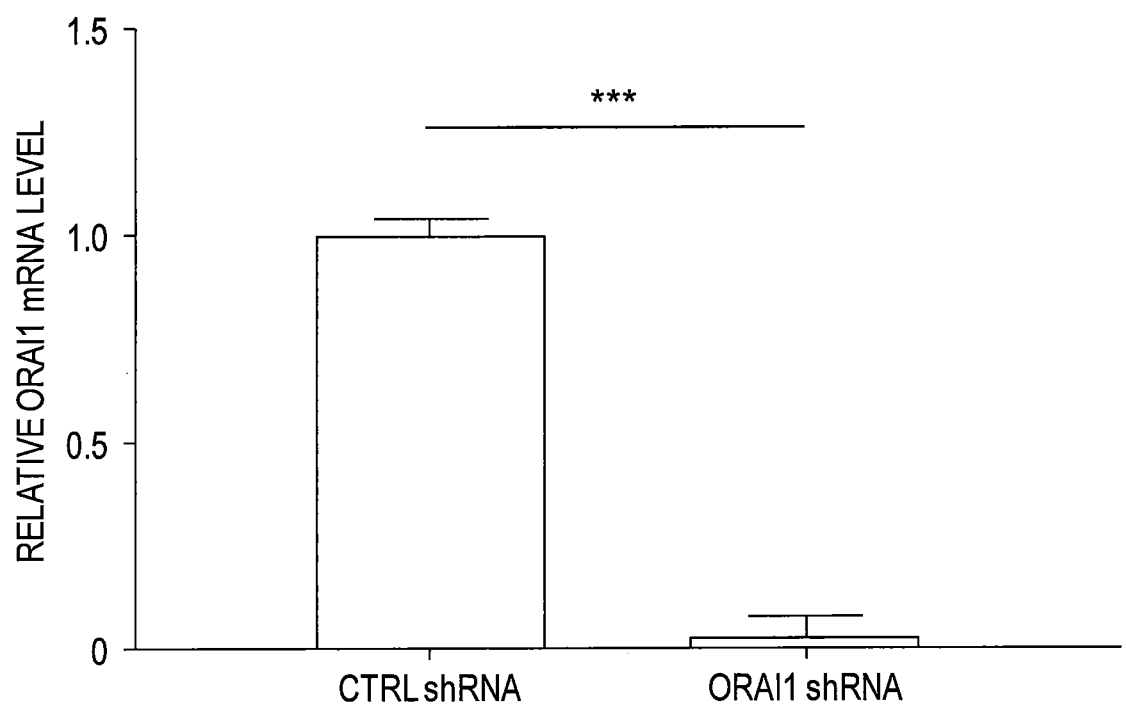
Figure 7G:
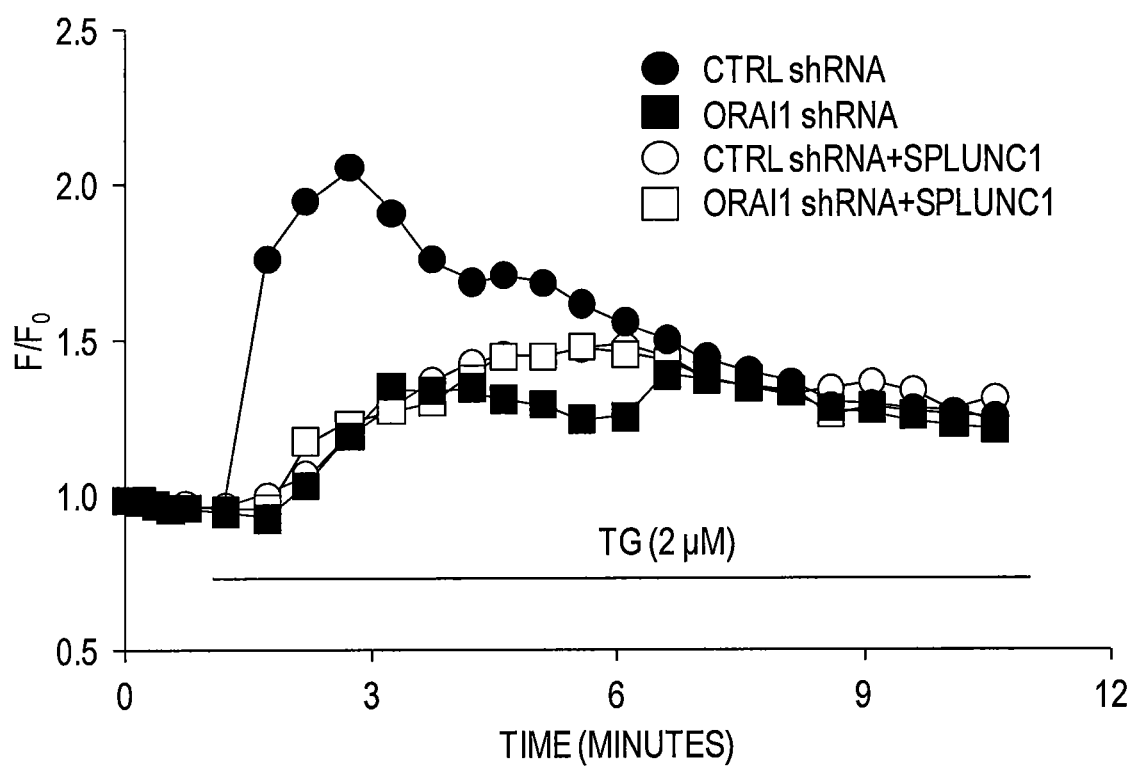
Figure 7H:
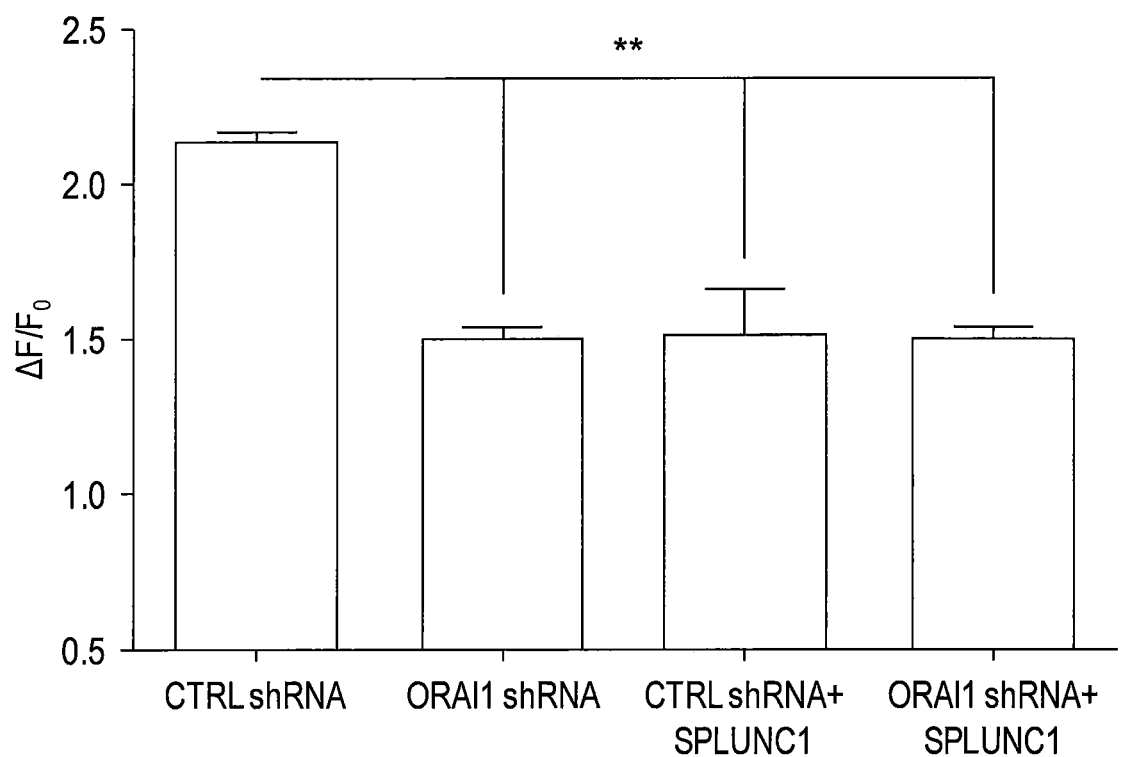

Since Orai1 mediates SOCE and is hyperactive in murine asthma models where SPLUNC1 is diminished (Spinelli et al., *Pflugers Archiv.: Eur. J. Physiol.* 464:481 (2012); Yang et al. *Exp. Physiol.* 97:1315 (2012)), it was tested whether these proteins interact. SPLUNC1 and Orai1, but not an alternate $Ca^{2+}$ channel (TRPC3), could be co-immunoprecipitated (FIGS. 7A, 7B and 8). Using ground state depletion super resolution microscopy, SPLUNC1 and Orai1 were found to co-localize in ASMC plasma membranes after 1 h incubation, and surface biotinylation/western blot and confocal microscopy demonstrated that plasma membrane Orai1 levels decreased by ~50% after 4 h of SPLUNC1 exposure (FIGS. 7C-7E). Meanwhile, cytosolic Orai1 increased, suggesting that binding with SPLUNC1 leads to subcellular localization change of Orai1 (FIGS. 9A-9B). To confirm that Orai1 is the target of SPLUNC1, endogenous Orai1 was knocked down in ASMC by shRNA, as confirmed by both qPCR (FIG. 7F) and immunoblot (FIG. 10). Orai1 knockdown decreased SPLUNC1 binding to ASMC plasma membranes (FIGS. 11A-11B and 12A-12B). Furthermore, the ability of SPLUNC1 to inhibit $Ca^{2+}$ signaling was lost when Orai1 was knocked down by shRNA, confirming that Orai1 was the target of SPLUNC1 (FIGS. 7G, 7H). A SPLUNC1 derived peptide (SEQ ID NO:2) inhibited thapsigargin-induced calcium release in human ASMC (FIG. 13). Taken together, these data suggest that SPLUNC1 binds to and inhibits Orai1 to block $Ca^{2+}$ influx in ASMC, resulting in a decrease in MLC phosphorylation and ASM contractility.

SPLUNC1 has previously been shown to regulate ENaC activity in airway epithelia by binding extracellularly to its β-subunit leading to channel internalization (Garcia-Caballero et al., *Proc. Natl. Acad. Sci. USA* 106:11412 (2009)). Here it is shown that basolaterally-secreted SPLUNC1 binds extracellularly to Orai1 leading to internalization inhibition of SOCE and a decrease in ASM contraction (FIGS. 7A-7H). It is noted that the S18 region, which regulates ENaC, is located at SPLUNC1's N-terminus (Tartan, et al., *Intl. J. Biochem. Cell Biol.* 52:130 (2014)), while α6 is at SPLUNC1's C-terminus; thus, these disparate functional regions are on opposing sides of SPLUNC1. The focus here is on basolaterally-secreted SPLUNC1's ability to regulate SOCE in ASM. However, the lack of SPLUNC1 may also have consequences for ENaC and Orai1 regulation in airway epithelia. Indeed, mucus has been shown to be dehydrated in asthmatic airways, which may indicate that ENaC is hyperactive, and ENaC regulation has been shown to be dysfunctional in asthma patients in vivo (Nakagami et al., *J. Immunol.* 181:2203 (2008); Rademacher et al. *Eur. Respiratory J.* 47:322 (2016); Loughlin et al., *Respiratory Med.* 104:29 (2010)). Furthermore, since mucus secretion is $Ca^{2+}$-dependent, increased SOCE in the absence of SPLUNC1 may contribute to the mucus hypersecretion phenotype seen in asthma.

Asthma is a chronic airway disease that is characterized by airflow limitation due to ASM contraction/AHR and mucus hypersecretion. The mucus hypersecretion component is likely due to Th2-driven goblet cell metaplasia (Cohn, *J. Clin. Invest.* 116:306 (2006); Erle et al., *J. Cell Biol.* 205:621 (2014)). As such, the transcription factors SAM-pointed domain-containing ETS-like factor (SPDEF) and forkhead ortholog A3 (FOXA3) are abnormally regulated in asthma leading to goblet cell metaplasia (Rajavelu et al., *J. Clin. Invest.* 125:2021 (2015); Chen et al., *Am. J. Respir. Crit. Care Med.* 189:301 (2014)). Whether SPDEF/FOXA3 activity is involved in reducing SPLUNC1 expression in asthmatic patients remains to be determined. Furthermore, while Chu et al. have shown that β-agonists, which are a common asthma treatment, can increase SPLUNC1 expression (Gross et al. *BMC Pulmonary Med.* 10:30 (2010)), a better understanding of how SPLUNC1 expression is regulated by β-agonists and other mainstream therapies including glucocorticoids may lead to novel, targeted therapies for treating asthma. Indeed, Chu et al. have demonstrated that SPLUNC1$^{(-/-)}$ mice have a more severe phenotype than WT mice, including eosinophilic inflammation, when sensitized by ovalbumin (Thaikoottathil et al., *Am. J. Respir. Cell Mol. Biol.* 47:253 (2012)). Chu et al. hypothesized that apically secreted SPLUNC1 "mopped up" excess bacterial lipopolysaccharide and did not factor in basolateral secreted SPLUNC1 into their model. As such, the present findings that SPLUNC1 is secreted basolaterally, where it can modulate SOCE and ASM contraction, are fundamentally novel advances that have important implications for asthma pathogenesis, providing a direct link between epithelial dysfunction and AHR, and for future new treatments for asthma.

Example 3

Immunosuppressive Effect of Ca-Regulating Peptides

To see whether the effects of the α6 peptides (SEQ ID NOS:2 and 3) extended beyond airway smooth muscle, the ability of these peptides to inhibit $Ca^{2+}$ influx in HEK293T cells was tested, since Orai1 has been shown to mediate $Ca^{2+}$ influx in HEK293T cells. HEK293T cells were grown in 384 well plates for 24 h, loaded with 10 mM Fluo4-AM for 30 min and then thapsigargin-induced $Ca^{2+}$ release was measured in the presence and absence of full length SPLUNC1 and the short (SEQ ID NO:3) and long (SEQ ID NO2) α6 peptides. Fluorescence (excitation at 488±5 nm, emission collected at 516±10 nm) was collected every 30 s using a Tecan Infinite Pro plate reader. Full dose response curves were performed for SPLUNC1 and the 2 peptides as shown in FIG. 14. As can be seen, both peptides showed similar inhibition of $Ca^{2+}$ influx as full length SPLUNC1.

To test whether α6 peptides were efficacious in vivo, a well-characterized murine allergy model was used, the house dust mite-exposed mouse (Wu T et al., *Nature Communications*, 2017). Since SPLUNC1$^{(-/-)}$ mice have asthma-like symptoms including spontaneous inflammation and airway hyperreactivity (Wu T et al., *Nature Communications*, 2017; Thaikoottathil et al., *Am. J. Respir. Cell Mol. Biol.* 47:253 (2012)), SPLUNC1$^{(-/-)}$ mice were exposed to 20 μg HDM intranasally on day 0 and day 14. After this time, they were challenged with 20 μg HDM intranasally from day 14 to day 17. 320 mM of the short α6 peptide was administered intranasally once per day on day 15 and on day 16 and sacrificed the animals were sacrificed on day 17. Bronchoalveolar lavage was performed and total and differential cell counts performed (FIG. 15). As can be seen, α6 peptide addition significantly reduced total cell count in HDM mice and also decreased neutrophil and eosinophil influx.

Immunoglobulin E (IgE) plays an important role in allergic hypersensitivity. Accordingly, it was next tested whether the α6 peptide could diminish circulating IgE levels. Using the same SPLUNC1$^{(-/-)}$ mice/HDM challenge as described in FIG. 15, serum was obtained on day 17 and IgE measured by ELISA. Consistent with the decrease in inflammatory cell numbers, it was found that α6 peptide addition significantly reduced plasma IgE levels (FIG. 16).

The foregoing is illustrative of the present invention, and is not to be construed as limiting thereof. The invention is defined by the following claims, with equivalents of the claims to be included therein.

That which is claimed is:

1. A method of inhibiting an immune response in a subject, comprising delivering to the subject a polypeptide or a functional fragment thereof comprising amino acids 235-249 of the amino acid sequence of SEQ ID NO:1, thereby inhibiting the immune response.

2. The method of claim 1, wherein the polypeptide or a functional fragment thereof consists essentially of the amino acid sequence of SEQ ID NO:2 or SEQ ID NO:3.

3. A method of inhibiting inflammation in a subject, comprising delivering to the subject a polypeptide or a functional fragment thereof comprising amino acids 235-249 of the amino acid sequence of SEQ ID NO:1, thereby inhibiting the inflammation.

4. The method of claim 3, wherein the polypeptide or a functional fragment thereof consists essentially of the amino acid sequence of SEQ ID NO:2 or SEQ ID NO:3.

5. A method of treating bronchitis, asthma, cystic fibrosis, or chronic obstructive pulmonary disease (COPD) in a subject in need thereof, comprising delivering to the subject a therapeutically effective amount of a polypeptide or a functional fragment thereof comprising amino acids 235-249 of the amino acid sequence of SEQ ID NO:1, thereby treating the autoimmune disease.

6. The method of claim 5, wherein the polypeptide or a functional fragment thereof consists essentially of the amino acid sequence of SEQ ID NO:2 or SEQ ID NO:3.

* * * * *

UNITED STATES PATENT AND TRADEMARK OFFICE
CERTIFICATE OF CORRECTION

PATENT NO. : 10,894,811 B2
APPLICATION NO. : 16/078397
DATED : January 19, 2021
INVENTOR(S) : Tarran et al.

Page 1 of 1

It is certified that error appears in the above-identified patent and that said Letters Patent is hereby corrected as shown below:

In the Specification

Column 3, Line 44: Please correct "in SPLUNC1$^{(-/-)}$ and SPLUNC1$^{(-/-)}$ litter" to read -- in SPLUNC1$^{(-/-)}$ and SPLUNC1$^{(+/+)}$ litter --

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office*